US009989412B2

(12) United States Patent
Rowlette et al.

(10) Patent No.: US 9,989,412 B2
(45) Date of Patent: Jun. 5, 2018

(54) LOW-NOISE SPECTROSCOPIC IMAGING SYSTEM

(71) Applicant: Daylight Solutions, Inc., San Diego, CA (US)

(72) Inventors: Jeremy Rowlette, Escondido, CA (US); Edeline Fotheringham, San Diego, CA (US); William Chapman, San Diego, CA (US); Miles Weida, Poway, CA (US); David Arnone, Mountain View, CA (US)

(73) Assignee: DAYLIGHT SOLUTIONS, INC., San Diego, CA (US)

( * ) Notice: Subject to any disclaimer, the term of this patent is extended or adjusted under 35 U.S.C. 154(b) by 238 days.

(21) Appl. No.: 15/081,743

(22) Filed: Mar. 25, 2016

(65) Prior Publication Data

US 2016/0209271 A1 Jul. 21, 2016

Related U.S. Application Data

(63) Continuation-in-part of application No. 14/353,487, filed as application No. PCT/US2012/061987 on Oct. 25, 2012, now Pat. No. 9,432,592.
(Continued)

(51) Int. Cl.
*H04N 9/47* (2006.01)
*G02B 13/14* (2006.01)
(Continued)

(52) U.S. Cl.
CPC ........... *G01J 3/0208* (2013.01); *G01J 3/0262* (2013.01); *G01J 3/0289* (2013.01); *G01J 3/08* (2013.01);
(Continued)

(58) Field of Classification Search
CPC ....... G01J 3/2823; G01J 3/0208; G01J 3/0202
See application file for complete search history.

(56) References Cited

U.S. PATENT DOCUMENTS 5,311,021 A * 5/1994 Messerschmidt .... G01N 21/255
250/339.07
8,115,993 B2 * 2/2012 Hauger .................. G02B 21/22
359/377
(Continued)

FOREIGN PATENT DOCUMENTS

WO WO2013063316 A1 5/2013
WO WO2014209471 A2 12/2014
(Continued)

OTHER PUBLICATIONS

U.S. Appl. No. 14/796,858, filed Jul. 10, 2015, with its entire prosecution and file history.

*Primary Examiner* — Tsion B Owens
(74) *Attorney, Agent, or Firm* — Roeder & Broder LLP; Steven G. Roeder

(57) ABSTRACT

A spectral imaging device (12) includes an image sensor (28), an illumination source (14), a refractive, optical element (24A), a mover assembly (24C) (29), and a control system (30). The image sensor (28) acquires data to construct a two-dimensional spectral image (13A) during a data acquisition time (346). The illumination source (14) generates an illumination beam (16) that illuminates the sample (10) to create a modified beam (16I) that follow a beam path (16B) from the sample (10) to the image sensor (28). The refractive, optical element (24A) is spaced apart a separation distance (42) from the sample (10) along the beam path (16B). During the data acquisition time (346), the control system (30) controls the illumination source (14) to generate the illumination beam (16), controls the mover assembly
(Continued)

(29) (24C) to modulate the separation distance (42), and controls the image sensor (28) to capture the data.

22 Claims, 13 Drawing Sheets

Related U.S. Application Data

(60) Provisional application No. 62/140,235, filed on Mar. 30, 2015, provisional application No. 61/551,147, filed on Oct. 25, 2011.

(51) Int. Cl.
| | |
|---|---|
| *G01J 3/02* | (2006.01) |
| *G01J 3/08* | (2006.01) |
| *G01J 3/10* | (2006.01) |
| *G01J 3/28* | (2006.01) |
| *G01J 3/32* | (2006.01) |
| *G01J 3/42* | (2006.01) |
| *G02B 21/16* | (2006.01) |
| *G02B 21/36* | (2006.01) |
| *G01N 21/39* | (2006.01) |
| *G01N 21/35* | (2014.01) |

(52) U.S. Cl.
CPC ............... *G01J 3/10* (2013.01); *G01J 3/2803* (2013.01); *G01J 3/32* (2013.01); *G01J 3/42* (2013.01); *G01N 21/39* (2013.01); *G02B 21/16* (2013.01); *G02B 21/361* (2013.01); *G01N 21/35* (2013.01)

(56) References Cited

U.S. PATENT DOCUMENTS

| | | | |
|---|---|---|---|
| 9,709,386 B1* | 7/2017 | Nicolaides | G01B 11/0641 |
| 2003/0227611 A1* | 12/2003 | Fein | G01N 1/2813 |
| | | | 356/36 |
| 2008/0018966 A1* | 1/2008 | Dubois | G01B 9/021 |
| | | | 359/9 |
| 2009/0213882 A1* | 8/2009 | Weida | G01N 21/3504 |
| | | | 372/23 |
| 2012/0206729 A1* | 8/2012 | Seligson | G03F 7/70633 |
| | | | 356/445 |
| 2013/0335797 A1* | 12/2013 | Cooper | G02B 21/16 |
| | | | 359/199.2 |
| 2014/0253714 A1 | 9/2014 | Weida | |
| 2015/0230702 A1* | 8/2015 | Uhlhorn | A61B 3/102 |
| | | | 351/206 |
| 2016/0018628 A1 | 1/2016 | Rowlette | |

FOREIGN PATENT DOCUMENTS

| | | |
|---|---|---|
| WO | WO2015109274 A1 | 7/2015 |
| WO | WO2016007925 A1 | 1/2016 |

\* cited by examiner

LOW-NOISE SPECTROSCOPIC IMAGING SYSTEM

RELATED APPLICATIONS

This application claims priority on U.S. Provisional Application No. 62/140,235 filed on Mar. 30, 2015, and entitled "LOW-NOISE SPECTROSCOPIC IMAGING SYSTEM". As far as permitted, the contents of U.S. Provisional Application No. 62/140,235, are incorporated herein by reference.

This application is a continuation in part of on U.S. application Ser. No. 14/353,487, and entitled "INFRARED IMAGING MICROSCOPE USING TUNABLE LASER RADIATION". U.S. application Ser. No. 14/353,487 is a national stage entry of PCT/US12/61987 filed on Oct. 25, 2012. PCT/US12/61987 claims priority on U.S. Provisional Application No. 61/551,147 filed on Oct. 25, 2011. As far as permitted, the contents U.S. application Ser. No. 14/353,487 are incorporated herein by reference.

Further, as far as permitted, the contents of PCT Application Serial No. PCT/US15/11884, filed on Jan. 18, 2015 and entitled "Low-Noise Spectroscopic Imaging System Using Substantially Coherent Illumination", are incorporated herein by reference.

GOVERNMENT SPONSORED DEVELOPMENT

The U.S. Government has rights in this invention pursuant to contract number NSF SBIR Phase I Award No. II-1046450 with the National Science Foundation.

BACKGROUND

Microscopes are often used to analyze a sample in order to evaluate certain details and/or properties of the sample that would not otherwise be visible to the naked eye. Additional information on the chemical properties of the sample can be obtained by illuminating and observing the sample with discrete optical frequencies of monochromatic laser radiation. Samples that can be analyzed this way include human tissue and cells, explosive residues, powders, liquids, solids, polymers, inks, and other materials. A human tissue sample may be analyzed for the presence of cancerous cells and/or other health related conditions. Other materials may be analyzed for the presence of explosive residues and/or other dangerous substances.

There is a never ending goal to improve the resolution and quality of the spectral images of the samples that are being generated.

SUMMARY

The present invention is directed to a spectral imaging device for generating a two-dimensional spectral image of a sample. The spectral imaging device includes an image sensor, an illumination source, an optical assembly, a mover assembly, and a control system. The image sensor includes a two-dimensional array of sensors that are used to acquire data to construct a two-dimensional spectral image. As provided herein, the image sensor acquires the spectral data used to construct one spectral image during a data acquisition time ("capture time"). The illumination source generates an illumination beam that illuminates the sample to create a modified beam that substantially follows a beam path from the sample to the image sensor. The optical assembly includes a refractive, optical element that is positioned along the beam path between the sample and the image sensor, the refractive optical element being spaced apart a separation distance from the sample along the beam path. The mover assembly moves at least one of the sample and the optical element along the beam path to change the separation distance. The control system (i) controls the illumination source to generate the illumination beam during the data acquisition time, (ii) controls the mover assembly to change the separation distance during the data acquisition time; and (iii) controls the image sensor to capture the data during the data acquisition time.

Changing of the separation distance during the capture of the spectral image modulates the working distance. As provided herein, this will frustrate the standing waves in the spectral system thereby decreasing noise and improving the quality and resolution of the spectral image.

In one embodiment, the mover assembly moves the sample relative to the refractive optical element along the beam path to adjust the separation distance. Alternatively, the mover assembly moves the refractive optical element relative to sample along the beam path to adjust the separation distance.

The illumination source can be tunable to adjust a center wavelength of the illumination beam. In one embodiment, the illumination source is a tunable laser source and the illumination beam is a laser beam.

The refractive, optical element includes a front element surface faces the sample. The front element surface can be curved and have a radius that is approximately equal to the separation distance. The front element surface can have a finite reflectivity to light near a center wavelength of the illumination beam.

As provided herein, the control system controls the mover assembly to adjust the separation distance by a modulation distance during the data acquisition time that is at least approximately three microns. Further, the control system can adjust an amplitude of the modulation distance as a function of wavelength of the illumination beam. Further, the control system can control the mover assembly to modulate the separation distance to have a frequency of at least approximately two times the data acquisition time.

In certain embodiments, the mover assembly can include a piezoelectric actuator that adjusts the separation distance.

Additionally, in certain embodiments, the control system controls the tunable illumination source to generate a plurality of discrete optical frequencies within a desired tuning range. In this embodiment, a separate spectral image can be captured during each discrete optical frequency.

Alternatively, the control system can control the tunable illumination source to generate a set of discrete optical frequencies near a different target optical frequency for each data acquisition time. In one, non-exclusive embodiment, the control system modulates the tunable light source to generate a set of discrete optical frequencies near a target optical frequency to produce a maximum optical frequency modulation, $\Delta v_{modulation}$, about the target optical frequency which satisfies the following prescription: $\Delta v_{modulation} = \pm \eta \Delta v / 2$, where $\eta$ is a constant having a value of greater than or equal to 0.1 and less than or equal to 100, and $\Delta v$ is the desired optical frequency spectral resolution. Stated in another fashion, the control system modulates the tunable light source to generate a set of discrete optical frequencies about and through a target optical frequency at an optical frequency modulation rate, and wherein the image sensor captures the output image during a capture time that is longer than the inverse of the optical frequency modulation rate.

In certain embodiments, tunable optical source emits a temporally coherent illumination beam and the desired tuning range is the mid-infrared range.

The present invention is also directed to a method for generating one or more spectral images, and a method for generating a spectral cube.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
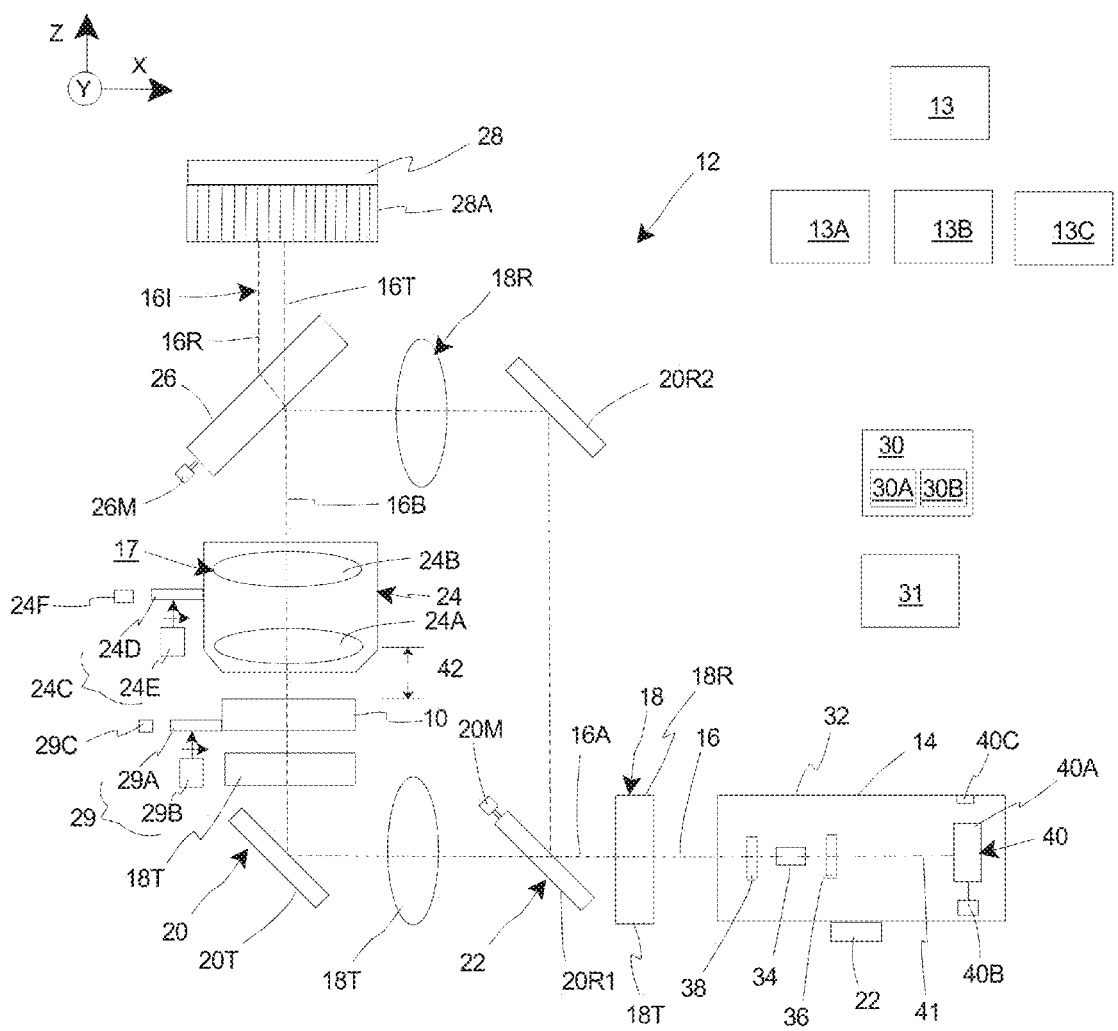
FIG. 1 is a simplified schematic illustration of a sample and an embodiment of a spectral imaging microscope having features of the present invention.

FIG. 1 is a simplified schematic illustration of a sample 10 and an embodiment of a spectral imaging device 12, e.g., a spectral imaging microscope, having features of the present invention. In particular, the spectral imaging device 12 can be used to quickly and accurately acquire a spectral cube 13 (illustrated as a box) of the sample 10 that can be used to analyze and evaluate the various properties of the sample 10. As provided herein, in certain embodiments, the spectral imaging device 12 is uniquely designed to generate a plurality of high resolution, two dimensional, output images 13A, 13B, 13C (only three are illustrated as boxes) of the sample 10 that are used to create the spectral cube 13 for the sample 10. The term "image" as used herein shall mean and include a two-dimensional photograph or screen display, or a two-dimensional array of data that can be used to generate the two-dimensional photograph or screen display.

As an overview, as discussed in greater detail herein below, the spectral imaging device 12 includes a mover assembly that selectively moves at least one of the sample 10 and an optical element 24A along a beam path 16B to change a separation distance ("Z") between the sample 10 and an optical element 24A during the capturing of one or more of the images 13A, 13B, 13C. Stated in another fashion, the present invention modulates a working distance of the spectral imaging device 12 during the capturing of the images 13A, 13B, 13C to frustrate the standing waves in the spectral imaging device 12. With this design, as provided herein, this will reduce the noise and improve the quality and resolution of the images 13A, 13B, 13C. Stated otherwise, changing the path length very quickly during the relatively slow data acquisition time of the image sensor 28 averages out the noise caused by the standing waves.

As provided herein, the sample 10 can be analyzed and evaluated in a static sense, i.e. where the properties of the sample 10 are substantially unchanged over the measurement period, and/or in a dynamic sense, i.e. where the properties of the sample 10 are evolving over the measurement period. In the static case, for each output image 13A, 13B, 13C, a one-dimensional spectra is produced for every pixel position of the respective, two-dimensional output image 13A, 13B, 13C to yield a three-dimensional spectral cube 13. In the dynamic case, a fourth dimension of time is added to yield a four-dimensional spectral matrix (not shown).

The fidelity of the data of the spectral cube 13 can be characterized by the repeatability of the spectral data at each pixel location, for each output image 13A, 13B, 13C over multiple trials. Each trial has a unique data collection start time. Because the source intensity may vary strongly across the sample 10 as well as across the optical frequency band of interest, one or more featureless background spectral cubes (without the sample) may be generated and used to normalize the signal spectral cube by taking the ratio of the signal spectral cube to the background spectral cube. If the frequencies are collected in an ordered array, then the ratio is referred to as the image transmittance.

As provided herein, in certain embodiments, a ratio of two background spectral cubes taken without the sample 10, at different times, can be used to produce a system transmittance spectral cube (not shown). Comparing the pixel-by-pixel transmittance over many trials and over optical frequencies is a suitable means for characterizing the intrinsic signal-to-noise ratio (SNR) of the spectral imaging device 12. A non-exclusive example of an acceptable measure of the intrinsic system SNR is the reciprocal of the root square mean (RSM) of the transmittance over a specified spectral range for two randomly selected spectral cube collection trials taken at different times.

The sample 10 can be a specimen that includes mammalian blood, mammalian blood serum, mammalian cells, mammalian tissue, mammalian biofluids, and their animal counterparts, plant matter, bacteria, polymers, hair, fibers, explosive residues, powders, liquids, solids, inks, and other materials commonly analyzed using spectroscopy and microscopy. More particularly, in certain non-exclusive applications, the sample 10 can include human blood serum, and the spectral imaging microscope 12 can be utilized for rapid screening of the serum specimen for the presence of disease and/or other health related conditions; and/or the spectral imaging microscope 12 can be utilized in certain forensic applications such as rapid screening of the sample 10 for the presence of explosive residues and/or other dangerous substances. Additionally, when positioned substantially within the spectral imaging microscope 12 for purposes of analysis, the sample 10 can be the specimen present by itself, or the sample 10 can include the specimen held in place using one or more slides (not shown), e.g., infrared transparent slides.

Further, the sample 10 can be thin enough to allow study through transmission of an illumination beam, e.g., an infrared illumination beam, through the sample 10 (i.e. in transmission mode), or the sample 10 can be an optically opaque sample that is analyzed through reflection of an illumination beam, e.g., an infrared illumination beam, by the sample 10 (i.e. in reflection mode). Still further, the sample 10 can be thin enough to allow study through transflection of an illumination beam, e.g., an infrared illumination beam can pass through the sample, reflect on the surface of a reflective substrate, and again pass through the sample 10, the illumination beam being double attenuated. For example, in the embodiment illustrated in FIG. 1, the spectral imaging microscope 12 can be utilized in transmission mode and/or reflection mode, and data can be acquired using a transmission, reflection, or transflection methodology.

It should be appreciated that the spectral imaging device 12 can be utilized in a variety of potential applications. For example, such applications can include, but are not limited to, spectral histopathology and cytopathology, hematology, pharmaceutical drug development and process control, detection of biochemical warfare agents and other hazardous materials, materials science, plasmonic sensors, and polymer science development.

The design of components of the spectral imaging device 12 can be varied to achieve the desired characteristics of the spectral imaging device 12. In one embodiment, the spectral imaging device 12 is an infrared spectral imaging microscope that uses tunable laser radiation to interrogate the sample 10.

In the non-exclusive embodiment illustrated in FIG. 1, the spectral imaging microscope 12 includes (i) an illumination source 14 that generates and/or emits an illumination beam 16, (ii) an optical assembly 17 that includes an illumination optical assembly 18 and an imaging optical assembly 24, (iii) a beam steerer assembly 20 that steers the illumination beam 16 along a desired beam path, (iv) an illumination switch 22 that is controlled by a user (not shown) so that the illumination beam 16 can be alternatively directed at the sample 10 in a transmission mode or a reflection mode, (v) a beam splitter 26, (vi) an image sensor 28 that captures information to create the output images 13A, 13B, 13C and the spectral cube 13 of the sample 10; (vii) a sample stage mover assembly 29 that retains and positions the sample 10; and (viii) a control system 30 that is electrically connected to and controls many of the components of the spectral imaging device 12. One or more of these devices can be referred to as a component.

It should be noted that the spectral imaging microscope 12 can be designed with more or fewer components than are illustrated in FIG. 1, and/or the components can be organized in another fashion than illustrated in FIG. 1. For example, the spectral imaging microscope 12 can include a multiple position lens turret (not shown) that includes one or more mid-infrared objective lens assemblies with different characteristics, and/or one or more objective lens assemblies that work outside the mid-infrared spectral range. Additionally, for example, the optical assembly 17 can be designed without the illumination optical assembly 18. Further, the illumination switch 22 can be eliminated if the spectral imaging device 12 is designed to only work in the transmission mode or the reflection mode.

Moreover, the spectral imaging device 12 can include an image display 31 (illustrated as a box), e.g. an LED display, that displays one or more of the output images 13A, 13B, 13C in real time, and/or subsequently displays the spectral cube 13.

In certain embodiments, the spectral imaging microscope 12 has a relatively high resolution, high numerical aperture ("NA"), and a relatively large field of view ("FOV"). This allows for the collection of data from relatively large samples. This will improve the speed in which the sample is analyzed. As one non-exclusive example, the spectral imaging microscope 12 can have NA of 0.7, a magnification of 12.5×, and a FOV of approximately 650 μm×650 μm, with a sample-referred pixel size of 1.36 μm. In another, non-exclusive example, the spectral imaging microscope 12 can have NA of 0.3, a magnification of 4×, and a FOV of approximately 2 millimeters×2 millimeters, with a sample-referred pixel size of 4.25 microns.

In certain embodiments, the illumination source 14 includes a laser source that emits a substantially temporally coherent illumination beam 16 (e.g. a laser beam) that is usable for illuminating and analyzing the sample 10 in transmission mode and/or in reflection mode. In FIG. 1, the illumination beam 16 is made up of a plurality of illumination rays 16A that follow the beam path 16B from the illumination source 14 to the sample 10 and from the sample 10 to the image sensor 28. Further, the illumination rays 16A can have a single, discrete center optical frequency that is within a desired tuning range of the illumination source 14. Alternatively, the illumination source 14 can be controlled by the control system 30 to vary the discrete center optical frequency of the illumination rays 16A over time within the desired tuning range.

As provided herein, the illumination beam 16 that illuminates the sample 10 to create a modified beam 16I that follow the beam path 16B from the sample 10 to the image sensor 28. The modified beam 16I can be considered to include a plurality of image rays that travel along the beam path 16B. The term beam path 16B shall mean the central beam propagation axis or path of the modified beam 16I as it travels from the sample 10 to the image sensor 28.

In certain, non-exclusive embodiments, the illumination beam 16 has a spectral width that is equal to or less than a desired spectral resolution (represented by the delta v "Δv") of the spectral imaging device 12. The builder of the spectral imaging device 12 can select the desired spectral resolution and build the system accordingly. For example, the desired spectral resolution of the spectral imaging device 12 can be four $cm^{-1}$ wavenumbers ($\Delta v = 4$ $cm^{-1}$). Alternatively, for example, the desired spectral resolution can be 2, 3, 4, 4.1, 5, 5.25, 6, 7, 8, 9, 10, or 16 $cm^{-1}$ wavenumbers. However, other desired spectral resolutions can be utilized.

In certain non-exclusive embodiments, the illumination source 14 is a tunable mid-infrared illumination source that directly generates and emits the illumination beam 16 having a center optical frequency that is in the mid-infrared ("MIR") range. In this example, the desired tuning range is the MIR range. Further, as used herein, term "MIR range" shall mean and include the spectral region or spectral band of between approximately two and twenty micrometers (2-20 μm) in wavelength or five thousand to 500 wavenumbers (5000-500 $cm^{-1}$). The mid-infrared range is particularly useful to spectroscopically interrogate the sample 10 since many samples 10 are comprised of molecules or groups of molecules that have fundamental vibrational modes in the MIR range, and thus present strong, unique absorption signatures within the MIR range. Alternatively, the illumination source 14 can be designed to generate the illumination beam 16 having a center optical frequency of greater than twenty or less than two micrometers.

Moreover, in alternative embodiments, the illumination source 14 can be either a pulsed laser or a continuous wave (CW) laser. For a pulsed illumination source 14, the illumination beam 16 will include a plurality of pulses of illumination rays 16A that follow the beam path 16B from the illumination source 14 to the sample 10 and from the sample 10 to the image sensor 28. Further, the pulses of illumination rays 16A can have a discrete center optical frequency that is within the MIR range.

In certain embodiments, the discrete center optical frequency of the illumination source 14 can vary over time over the entire or a portion of the MIR range to analyze the sample 10 over the desired spectral range. For example, for a pulsed illumination source 14, the illumination source 14 can be tuned to generate an illumination beam 16 that consists of a set of sequential, specific output pulses of light having different, discrete center optical frequency that span the entire or just a portion of the MIR range. For example, the illumination source 14 can be tuned to a first position and one or more pulses can be generated having approximately the same first center optical frequency ("first target optical frequency"). Subsequently, the illumination source 14 can be tuned to a second position and one or more pulses can be generated having approximately the same second center optical frequency ("second target optical frequency") that is different from the first center optical frequency. Next, the illumination source 14 can be tuned to a third position and one or more pulses can be generated having approximately the same third center optical frequency ("third target optical frequency") that is different from the first and second center optical frequency. This process can be repeated to a plurality of additional target optical frequencies throughout a portion or the entire MIR range. As non-exclusive examples, the number of pulses at each discrete optical frequency can be 1, 5, 10, 50, 100, 200, 500, 1000, 10,000 or more. Alternatively, the illumination source 14 can be operated in a continuous wave fashion at each target optical frequency.

The number of discrete target optical frequencies in the set used to acquire the spectral images 13A-13C used to create the spectral cube 13 can also vary according to the sample 10. As non-exclusive examples, the number of discrete target optical frequencies in the mid-infrared range utilized to create the spectral cube 13 can be approximately 1, 2, 3, 4, 5, 6, 7, 8, 9, 10, 15, 20, 25, 40, 200, 226, 400, 552 or 4000. As provided herein, the term "target optical frequency step" shall mean the smallest allowed difference between adjacent target optical frequencies. In alternative, non-exclusive embodiments, the target optical frequency step can be approximately 0.1, 0.2, 0.25, 0.33, 0.5, 0.67, 0.7, 1.0, 2.0, 4.0, 8.0, or 16, wavenumbers.

In certain, non-exclusive embodiments, the illumination beam 16 from the MIR illumination source 14 has an optical spectral full width at half maximum (FWHM) of less than approximately 0.01, 0.05, 0.1, 0.25, 0.5, 1.0, 2.0, or 4 $cm^{-1}$.

In certain embodiments, the control system 30 can control the illumination source 14 to be tuned so that the illumination beam 16 has the first target optical frequency, and the control system 30 can control the image sensor 28 to capture the first spectral image 13A with the sample 10 illuminated at the first target optical frequency during a first data acquisition time. Subsequently, the control system 30 can control the illumination source 14 to be tuned so that the illumination beam 16 has the second target optical frequency and the control system 30 can control the image sensor 28 to capture the second spectral image 13B with the sample 10 illuminated at the second target optical frequency during a second data acquisition time. This process is repeated for each target optical frequency until a plurality of spectral images 13A, 13B, 13C, are collected across the optical frequency range of interest, thus generating a spectral cube 13.

Additionally, the illumination source 14 of FIG. 1 can include multiple individual lasers that span a portion or all of the desired mid-infrared spectral range. A description of an illumination source 14 that includes multiple individual lasers is described in U.S. Pat. No. 9,086,375, entitled "Laser Source With A Large Spectral Range" which issued on Jul. 21, 2015. As far as permitted, the contents of U.S. Pat. No. 9,086,375 are incorporated herein by reference. The illumination source 14 can utilize a variety of methods to rapidly switch between the target optical frequencies. These include techniques such as rapid tuning mechanisms, galvo-controlled mirrors to switch between different laser modules, or spectral beam combining techniques of multiple laser modules and subsequent time-division multiplexing of laser illumination.

In one, non-exclusive embodiment, the illumination source 14 is an external cavity laser that includes a rigid laser frame 32, a gain medium 34, a cavity optical assembly 36, an output optical assembly 38, and a wavelength selective ("WS") feedback assembly 40 (e.g., a movable grating).

The design of the gain medium 34 can be varied pursuant to the teachings provided herein. In one, non-exclusive embodiment, the gain medium 34 directly emits the illumination beam 16 without any frequency conversion. As a non-exclusive example, the gain medium 34 can be a semiconductor type laser. As used herein, the term semiconductor shall include any solid crystalline substance having electrical conductivity greater than insulators but less than good conductors. More specifically, in certain embodiments, the gain medium 34 is a Quantum Cascade (QC) gain medium, an Interband Cascade (IC) gain medium, or a mid-infrared diode. Alternatively, another type of gain medium 34 can be utilized.

In FIG. 1, the gain medium 34 includes (i) a first facet that faces the cavity optical assembly 36 and the WS feedback assembly 40, and (ii) a second facet that faces the output optical assembly 38. In this embodiment, the gain medium 34 emits from both facets. In one embodiment, the first facet is coated with an anti-reflection ("AR") coating and the second facet is coated with a reflective coating. The AR coating allows light directed from the gain medium 34 at the first facet to easily exit the gain medium 34 as an illumination beam directed at the WS feedback assembly 40; and allows the illumination beam reflected from the WS feedback assembly 40 to easily enter the gain medium 34.

The illumination beam 16 exits from the second facet. The reflective coating on the second facet reflects at least some of the light that is directed at the second facet from the gain medium 34 back into the gain medium 34. In one non-exclusive embodiment, the AR coating can have a reflectivity of less than approximately 2 percent, and the reflective coating can have a reflectivity of between approximately 2-95 percent. In this embodiment, the reflective coating acts as an output coupler (e.g., a first end) for the external cavity.

The cavity optical assembly 36 is positioned between the gain medium 34 and the WS feedback assembly 40 along a lasing axis 41, and collimates and focuses the light that passes between these components. For example, the cavity optical assembly 36 can include a single lens or more than one lens. For example, the lens can be an aspherical lens having an optical axis that is aligned with the lasing axis. In one embodiment, to achieve the desired small size and portability, the lens has a relatively small diameter. The lens can comprise materials selected from the group of Ge, ZnSe, ZnS, Si, CaF2, BaF2 or chalcogenide glass. However, other materials may also be utilized.

The output optical assembly 38 is positioned along the lasing axis 41. In this design, the output optical assembly 38 collimates and focuses the illumination beam 16 that exits the second facet of the gain medium 34. For example, the output optical assembly 38 can include a single lens or more than one lens that are somewhat similar in design to the lens of the cavity optical assembly 36.

The WS feedback assembly 40 reflects the light back to the gain medium 34, and is used to precisely select and adjust the lasing frequency (wavelength) of the external cavity and the center optical frequency of the illumination beam 16. Stated in another fashion, the WS feedback assembly 40 is used to feed back to the gain medium 34 a relatively narrow band optical frequency which is then amplified in the gain medium 34. In this manner, the illumination beam 16 may be tuned with the WS feedback assembly 40 without adjusting the gain medium 34. Thus, with the external cavity arrangements disclosed herein, the WS feedback assembly 40 dictates what optical frequency will experience the most gain and thus dominate the optical frequency of the illumination beam 16.

A number of alternative embodiments of the WS feedback assembly 40 can be utilized. In FIG. 1, the WS feedback assembly 40 is spaced apart from the gain medium 34 and defines a second end of the external cavity. In this embodiment, the external cavity extends from the output coupler (reflective coating) on the second facet to the WS feedback assembly 40. The term external cavity is utilized to designate the WS feedback assembly 40 is positioned outside of the gain medium 34.

In some embodiments, the WS feedback assembly 40 includes a diffraction grating 40A and a grating mover 40B that selectively moves (e.g., rotates) the diffraction grating 40A to adjust the lasing frequency of the gain medium 34 and the optical frequency of the illumination beam 16. The diffraction grating 40A can be continuously monitored with a grating measurement system 40C (e.g. an encoder) that provides for closed loop control of the grating mover 40B. With this design, the optical frequency of the illumination beam 16 can be selectively adjusted in a closed loop fashion so that the sample 10 can be imaged at many different, precise, selectively adjustable optical frequencies throughout a portion or the entire MIR spectrum.

The control system 30 controls the operation of the illumination source 14 including the electrical power to the grating mover 40B, and the electrical power that is directed to the gain medium 34 (e.g., controls the gain medium 34 by controlling the electron injection current). Further, the control system 30 can control the image sensor 28 to control the timing of the capture of the images 13A, 13B, 13C. In certain embodiments, the control system 30 (i) controls the illumination source 14 to generate the illumination beam 16 during the data acquisition time, (ii) controls the mover assembly to change the separation distance during the data acquisition time; and (iii) controls the image sensor 28 to capture the data during the data acquisition time. For example, the control system 30 can include one or more processors 30A (illustrated as a box) and/or electronic data storage devices 30B (illustrated as a box).

The collection of an accurate spectral cube 13 requires that the optical frequency of the optical illumination beam be precisely known as the laser is tuned. In certain embodiments, the control system 30 directs the pulses of power to the gain medium 34 based on the position signal received from the grating measurement system 40C. Stated in another fashion, the control system 30 can direct one or more pulses of power to the gain medium 34 at each of the plurality of alternative device positions so that the laser generates the set of discrete target optical frequencies. In this embodiment, the control system 30 can direct one or more pulses of power to the gain medium 34 upon receipt of each new position signal. As a result thereof, the specific optical frequency of the pulses will not be influenced by variations in speed of the grating mover 40B.

The duration of each pulse of power directed by the control system 30 to the gain medium 34 can also be varied. In alternative, non-exclusive embodiments, the control system 30 can control each pulse of power to have a duration of approximately 10, 25, 50, 75, 100, 150, 200, 300, 400, 500, 600 or 700 nanoseconds.

Once the illumination source 14 has emitted the illumination beam 16, the illumination beam 16 is directed toward the sample 10 so that the sample 10 may be properly and effectively illuminated by the illumination beam 16. For example, when the spectral imaging microscope 12 is operating in transmission mode, the illumination beam 16 is directed toward the sample 10 in order to properly and effectively illuminate the sample 10. In this example, the illumination rays 16A that are transmitted through the sample 10 are referred to as transmitted rays 16T.

In another example, when the spectral imaging microscope 12 is operating in reflection mode, the illumination beam 16 is directed toward the sample 10 in order to properly and effectively illuminate the sample 10. In this example, the illumination rays 16A that are reflected off of the sample 10 are referred to as reflected rays 16R.

It should be noted that path of the beams in both transmission mode and the reflection mode are illustrated in FIG. 1. Stated in another fashion, in FIG. 1, (i) the path of the illumination beam 16 to the sample 10 and the transmitted rays 16T to the image sensor 28 in the transmission mode; and (ii) the alternative path of the illumination beam 16 to the sample 10 and the reflected rays 16R to the image sensor 28 in the reflection mode are both shown. However, in certain embodiments, the spectral imaging device 10 can only be used in the transmission mode or the reflection mode at any given time.

In the embodiment illustrated in FIG. 1, when operating in transmission mode, the illumination beam 16 exiting the illumination source 14 is directed with a portion of the illumination optical assembly 18, i.e. a transmission illumination optical assembly 18T, toward the sample 10 so as to impinge on the sample 10. In one embodiment, the transmission illumination optical assembly 18T can include one or more optical, refractive elements, e.g., lenses and/or windows (three such refractive optical elements are illustrated in FIG. 1), that direct the illumination beam 16 at the sample 10. Further, in certain embodiments, the refractive elements are operable in the MIR range. The optical, refractive elements can comprise materials selected from the group of Ge, ZnSe, ZnS, Si, CaF2, BaF2 or chalcogenide glass. However, other materials may also be utilized.

In certain embodiments, the transmission illumination optical assembly 18T can be used to transform, i.e. to increase (magnify) or decrease, the size and profile of the illumination beam 16 to match and simultaneously illuminate a desired transmission illuminated area on the sample 10. Stated another way, the transmission illumination optical assembly 18T can be used to condition and focus the illumination beam 16 so that the illumination beam 16 has the correct or desired size and beam profile on the sample 10. In certain embodiments, the size of the transmission illuminated area of the sample 10 is tailored to correspond to the design of the image sensor 28 and the imaging optical assembly 24. As non-exclusive examples, the desired transmission illuminated circular area bounded by a diameter that is approximately 50, 100, 200, 250, 500, 600, 650, 700, 1000, or by 2000 microns.

In the embodiment illustrated in FIG. 1, the spectral imaging microscope 12 and/or the illumination optical assembly 18 can also include a reflection illumination optical assembly 18R for directing the illumination beam 16 at the sample 10 when operating in reflection mode. In one embodiment, the reflection illumination optical assembly 18R includes one or more optical, refractive elements, e.g., lenses and/or windows, that direct the illumination beam 16 at the sample 10. In this embodiment, the refractive elements can be operable in the MIR range. The optical, refractive elements can comprise materials selected from the group of Ge, ZnSe, ZnS, Si, CaF2, BaF2 or chalcogenide glass. However, other materials may also be utilized.

Additionally, in certain embodiments, the reflection illumination optical assembly 18R can be used to transform, i.e. to increase (magnify) or decrease, the size and profile of the illumination beam 16 to match a desired reflection illuminated area on the sample 10. Stated another way, the reflection illumination optical assembly 18R can be used to condition and focus the illumination beam 16 so that the illumination beam 16 has the desired beam profile on the sample 10. As non-exclusive examples, the desired reflection illuminated area is approximately a circular area bounded by a diameter that is approximately 50, 100, 200, 250, 500, 600, 650, 700, 1000, or by 2000 um.

As noted above, the beam steerer assembly 20 is utilized to steer the illumination beam 16 such that the illumination beam 16 can be alternatively utilized in transmission mode or reflection mode. The design of the beam steerer assembly 20 can be varied. In one embodiment, the beam steerer assembly 20 includes a plurality of beam steerers 20T, 20R1, 20R2, e.g. mirrors (reflective in the desired optical frequency spectrum), which are positioned so as to redirect the path of the illumination beam 16 by approximately ninety degrees. Alternatively, the beam steerer assembly 20 can have a different design and/or the beam steerers 20T, 20R1, 20R2 can be positioned so as to redirect the path of the illumination beam 16 by greater than or less than approximately ninety degrees. Still alternatively, the beam steerers 20T, 20R1, 20R2 can include a curved mirror that reflects and conditions the illumination beam 16 (i) to complement the illumination optical assembly 18, or (ii) to allow for the elimination of a portion or all of the illumination optical assembly 18. Furthermore, the beam steerer assembly may also include one or more electrically controllable angular adjustments.

For example, in the embodiment illustrated in FIG. 1, when utilized in transmission mode, the illumination beam 16 only impinges on a single transmission beam steerer 20T before being directed toward the sample 10. Additionally and/or alternatively, in this embodiment, when utilized in reflection mode, the illumination beam impinges on two reflection beam steerers, i.e. a first reflection beam steerer 20R1 and a second reflection beam steerer 20R2, before being directed toward the sample 10.

It should be appreciated that, in this embodiment, the first reflection beam steerer 20R1, which is positioned between the illumination source 14 and the transmission beam steerer 20T, includes a steerer mover 20M that can be controlled by the control system 20 to selectively move the first reflection beam steerer 20R1 into and out of the way of the illumination beam 16. With this design, the reflection beam steerer 20R1 and the steerer mover 20M function as an illumination switch 22 that determines if the spectral imaging device 12 is used in transmission mode or reflectance mode. In this embodiment, when the spectral imaging device 12 is being used in transmission mode, the first reflection beam steerer 20R1 can be selectively moved out of the beam path so that the illumination beam 16 does not impinge on the first reflection beam steerer 20R1.

Thus, the illumination switch 22 enables the spectral imaging microscope 12 to selectively switch between transmission mode and reflection mode. In particular, in this embodiment, the illumination switch 22 can be utilized to selectively activate the steerer mover 20M to move the first reflection beam steerer 20R1 into and out of the path of the illumination beam 16, i.e. when the spectral imaging microscope 12 is being utilized in transmission mode; or to move the first reflection beam steerer 20R1 into the path of the illumination beam 16, i.e. when the spectral imaging microscope 12 is being utilized in reflection mode.

Moreover, in reflection mode, as illustrated in FIG. 1, the illumination beam 16 is directed at the sample 10 with the beam splitter 26. The design of the beam splitter 26 can be varied to suit the specific requirements of the spectral imaging microscope 12. In certain embodiments, the beam splitter 26, e.g., a fifty percent (50%) beam splitter, can redirect (reflect) a first portion of the illumination beam 16 toward the sample 10, and transmit a second portion (not shown) of the illumination rays 16A of the illumination beam 16. Alternatively, the beam splitter 26 can be a different percentage. The second portion of the illumination beam 16 is subsequently directed away from the system and not used by the spectral imaging microscope 12. It should be noted that the second (or discarded) portion of the illumination beam 16 that is generated from this first pass through the beam splitter 26 is not shown in FIG. 1A for purposes of clarity.

In certain embodiments, the beam splitter 26 can be made from a variety of infrared transmissive materials, such as ZnSe or Ge, or other materials. Additionally, the beam splitter 26 can be a plano-piano beam splitter, with one side anti-reflection (AR) coated, and the other coated or uncoated for partial reflectivity. The beam splitter 26 can also provide lensing action for transforming the illumination beam 16 as desired. The beam splitter 26 can also incorporate design elements to eliminate first and second surface interference effects due to the coherent nature of the illumination beam 16. As non-exclusive examples, design elements that would reduce the surface interference effects include anti-reflective coatings (for the optical frequency of the beam), wedged elements, and/or curved optical surfaces.

Further, as shown in the embodiment illustrated in FIG. 1, the modified beam 16I (i.e. the transmitted beam (or rays) 16T or the reflected beam (or rays) 16R), that are collected and focused by the objective lens assembly 24 are directed at the beam splitter 26. In this embodiment, if the beam splitter 26 is a fifty percent (50%) beam splitter, the transmitted beam 16T or the reflected beam 16R can be split into (i) the imaged rays 16I that are imaged on the image sensor 28, and (ii) discarded rays that are directed away from the image sensor 28.

Alternatively, the beam splitter 26 can include a splitter mover 26M that can be controlled by the control system 20 to selectively move the beam splitter 26 into and out of the way of the imaged rays 16I between the objective lens assembly 24 and the image sensor 28. With this design, when the spectral imaging device 12 is being used in transmission mode, the beam splitter 26 can be selectively moved out of the beam path so that the transmitted rays 16T travel directly from the objective lens assembly 24 to the image sensor 28. Alternatively, when the spectral imaging device 12 is being used in reflection mode, the beam splitter 26 can be selectively moved into the beam path so that the illumination beam 16 is directed towards the objective lens assembly 24 and the sample 10. Subsequently, the reflected rays 16R from the sample 10 are partly transmitted through the beam splitter 26 to the image sensor 28.

The imaging optical assembly 24 can have any suitable design depending on the specific requirements of the spectral imaging microscope 12. When the illumination rays 16A of the illumination beam 16 are illuminating the sample 10 in transmission mode, at least a portion of the transmitted rays 16T that are transmitted through the sample 10 are received by the imaging optical assembly 24 and imaged on the image sensor 28. Somewhat similarly, when the illumination rays 16A of the illumination beam 16 are illuminating the sample 10 in reflection mode, at least a portion of the reflected rays 16R that are reflected from the sample 10 are received by the imaging optical assembly 24 and imaged on the image sensor 28. Stated in another fashion, the imaging optical assembly 24 receives at least a portion of the transmitted rays 16T that are transmitted through the sample 10, or at least a portion of the reflected rays 16R that are reflected from the sample 10 and forms an image on the image sensor 28.

As utilized herein, the term "imaged rays" 16I shall mean the transmitted rays 16T or the reflected rays 16R that are collected by the imaging optical assembly 24 and imaged on the image sensor 28. As provided herein, the imaging optical assembly 24 receives the imaged rays 16I from a plurality of points on the sample 10 and forms the image on the image sensor 28. The imaged rays 16I travel along the beam path 16B from the sample 10 to the image sensor 28.

In one embodiment, the imaging optical assembly 24 can include a first refractive element 24A and a second refractive element 24B that cooperate to form an image of the sample 10 on the image sensor 28. The refractive elements 24A, 24B can be spaced apart. Alternatively, the imaging optical assembly 24 can include greater than two refractive elements or only one refractive element. It should be noted that the first refractive element 24A can also be referred to as a "front, refractive optical element", a "proximal, refractive optical element", or a "last, refractive optical element" because it is the closest element of the imaging optical assembly 24 to the sample 10. In certain embodiments, the first refractive element 24A is the closest optical element that is positioned between the sample 10 and the image sensor 28, while still being spaced apart from the sample 10. Further, the first refractive element 24A can be coaxial with the beam path 16B.

As provided herein, the first refractive element 24A is spaced apart from the sample 10 a separation distance 42 along the beam path 16B between the sample 10 and the first refractive element 24A. The phase separation distance 42 can also be referred to as a working distance or "z".

In one embodiment, the first refractive element 24A can be an objective lens that collects the imaged rays 16I, and focuses the imaged rays 16I on the image sensor 28.

Moreover, as illustrated, the first refractive element 24A is positioned substantially between the sample 10 and the second refractive element 24B. Additionally, in one embodiment, the second refractive element 24B can be a projection lens that projects the imaged rays 16I toward the image sensor 28. Moreover, as illustrated, the second refractive element 24B is positioned substantially between the first refractive element 24A and the image sensor 28. Further, in certain embodiments, each of the refractive elements 24A, 24B can be refractive in the MIR range and/or the optical frequency of the illumination beam 16.

Each of the refractive elements 24A, 24B in the spectral imaging device 12 is operative in the desired tuning range of the spectral imaging device 12 and can be types such as plano-convex, plano-concave, meniscus, and aspherical, as well as other types. For refractive lenses in the MIR range, materials such as Ge, ZnSe, ZnS, Si, CaF, BaF or chalcogenide glass and other materials can be employed. Reflective lenses can be elliptical, paraboloid, or other shapes. The reflective surface can be dichroic coating, Au, Ag, or other surface types.

Still further, one or both of the refractive elements 24A, 24B can be a compound lens. Moreover, as described in greater detail herein below, pursuant to the teachings of the present invention, the refractive elements 24A, 24B can have thicknesses and spacing (i.e. separation) that inhibit wavelength-dependent noise, e.g., parasitic etalon modulations, from adversely impacting the image quality and optical spectral resolution of the spectra generated from the set of wavelength dependent spectral images 13A, 13B, 13C of the sample 10 that are being generated.

In one embodiment, each refractive element in the spectral imaging device 12 has an element optical thickness, t, that is defined by either $t \geq 1/(2n\Delta v)$ or $t \leq 1/(2n(v_2-v_1))$; and the spacing (separation distance, d) between adjacent refractive elements is defined by either $d \geq 1/(2n\Delta v)$ or $d \leq 1/(2n(v_2-v_1))$; where n is refractive index of the respective refractive element, $\Delta v$ is the desired spectral resolution, $v_1$ is a lower bound of the desired tuning range, and $v_2$ is an upper bound of the desired tuning range. Alternatively, each refractive element is defined by both $t \geq 1/(2n\Delta v)$ or $t \leq 1/(2n(v_2-v_1))$; and the spacing (separation distance, d) is defined by both $d \geq 1/(2n\Delta v)$ or $d \leq 1/(2n(v_2-v_1))$.

It should be appreciated that the fluid, e.g., air or another suitable fluid that fills the spacing between the refractive elements 24A, 24B, and the spacing between the refractive elements 24A, 24B and the image sensor 28 also function as optical elements that can be refractive in the MIR range.

In various embodiments, the image sensor 28 can include a two-dimensional array of sensor elements 28A that are used to capture information used to construct a two-dimensional image 13A-13C including the two dimensional array of data (data at each pixel). As provided herein, the image sensor 28 is designed and/or controlled by the control system 30 to capture the information for each image 13A-13C during a separate data acquisition time. Stated in another example, the image sensor 28 can be controlled to have a certain data acquisition rate. Non-exclusive examples of suitable data acquisition rates for the image sensor 28 include thirty, sixty, one hundred and twenty, or two hundred and forty hertz. However, other data acquisition rates can be utilized.

Additionally, the design of the image sensor 28 can be varied to correspond to the optical frequency range of the illumination beam 16, i.e. of the modified beam 16I. For example, for a MIR beam 16, the image sensor 28 can be an infrared camera that includes an image sensor that senses infrared light and converts the infrared light into an array of electronic signals that represents an image of the sample. Stated in another fashion, if the illumination beam 16 is in the MIR range, the image sensor 28 can be a MIR imager. More specifically, if the illumination beam 16 is in the infrared spectral region from two to twenty μm, the image sensor 28 is sensitive to the infrared spectral region from two to twenty μm.

Non-exclusive examples of suitable infrared image sensors 28 include (i) vanadium oxide (VOX) and amorphous silicon microbolometer arrays such as the FPA in the FLIR Tau 640 infrared camera that are typically responsive in the seven to fourteen μm spectral range; (ii) mercury cadmium telluride (HgCdTe or MCT) arrays such as those in the FLIR Orion SC7000 Series cameras that are responsive in the 7.7 to 11.5 μm spectral range; (iii) indium antimonide (InSb) arrays such as those in the FLIR Orion SC7000 Series cameras that are responsive in the 1.5 to 5.5 μm spectral range; (iv) indium gallium arsenide (InGaAs); (v) uncooled hybrid arrays involving $VO_x$ and other materials from DRS that are responsive in the two to twenty μm spectral range; or (vi) any other type of image sensor that is designed to be sensitive to infrared light in the two to twenty μm range and has electronics allowing reading out of each element's signal level to generate a two-dimensional array of image information (data).

In one specific embodiment, the image sensor 28 is a microbolometer that includes a two-dimensional array of photosensitive elements (pixels) 28A that are sensitive to the optical frequency of the illumination beam 16. Stated in another fashion, in one embodiment, the image sensor 28 is a micro-electromechanical systems (MEMS) device fabricated in such a way as to create a plurality of small bolometer pixel elements that is thermally isolated from the underlying substrate. The spacing between the pixel elements is referred to as the pitch of the array. As non-exclusive examples, the two-dimensional array can include approximately 640×480; 320×240; 480×480; 80×60; 1080× 720; 120×120; 240×240; or 480×640 pixels. It should be noted that the information from the pixels can be used to generate the output images 13A, 13B, 13C and/or the spectral cube 13.

During use of the spectral imaging device 12, it is desired to improve the spectral resolution and quality of the two-dimensional data of images 13A-13C of the sample 10 and the spectral cube 13. More specifically, in various applications, it is desired to inhibit various noise sources from adversely impacting the quality of the two-dimensional data of the images 13A, 13B, 13C of the sample 10 that are being generated.

Unfortunately, in real systems, various random and systematic noise sources may exist which can cause a diminished and/or undesired SNR. Examples of random noise sources include, but are not limited to, quantum (Shot) and thermal (Johnson) noise in the image sensor 28, amplitude and frequency fluctuations of the illumination source, and random fluctuations in the transmittance of components contained within the spectral imaging device 12. Examples of systematic noise sources include, but are not limited to, the drift in illumination intensity, frequency, and the directional pointing of the source between trials.

An additional wavelength-dependent noise source in spectroscopic imaging systems can arise as a result from multiple reflections from surfaces and edges of the refractive elements within the spectral imaging device 12. For spectral imaging devices 12 which employ temporally coherent optical sources 14 such as a laser or optically filtered broad band sources, the complex electric fields of the multiple reflected beams will add coherently to produce an optical frequency dependent transmittance as a result of constructive and destructive interference.

As provided herein, in certain embodiments, the present invention provides that the noise from the multiple reflections from surfaces and edges of the refractive elements within the spectral imaging device 12 can be reduced by modulating the separation distance 42 between the first refractive element 24A and the sample 10 during the capturing of each spectral image 13A-13C. As alternative examples, (i) the first refractive element 24A can be moved relative to the sample 10 to modulate the separation distance 42, (ii) the sample 10 can be moved relative to the first refractive element 24A to modulate the separation distance 42, or (iii) both the first refractive element 24A and the sample 10 can be moved to modulate the separation distance 42.

The sample stage mover assembly 29 retains and positions the sample 10. In certain embodiments, the sample stage mover assembly 29 includes a sample stage 29A that retains the sample 10, and a sample stage mover 29B that selectively moves the sample stage 29A and sample 10 under the control of the control system 30. Additionally, the sample stage mover assembly 29 can include a sample stage measurement system 29C (e.g. one or more encoders, interferometers, capacitance sensor(s), electrical sensors, optical sensors, or another type of sensors) that monitors the position of the sample stage 29A and the sample 10 relative to the optical element 24A or another reference, and provides that information to the control system 30. This allows for closed loop positional control of the sample stage 29A with the control system 30. Stated in another fashion, the sample stage measurement system 29C can provide feedback that relates to the separation distance 42, and the control system 30 can use this feedback to control the sample stage mover assembly 29 in a closed loop fashion. It should be noted that the sample stage 29A, the sample stage mover 29B, and the stage measurement system 29C are illustrated as simplified boxes, but will have a much different design that than illustrated in FIG. 1.

In one non-exclusive embodiment, the sample stage mover 29B is controlled to move the sample stage 29A and sample 10 along the beam path 16B to modulate the separation distance 42 during the data acquisition time in which the image sensor 28 is controlled to construct the two-dimensional image 13A, 13B, 13C. Stated in another fashion, the stage assembly 29 is controlled to adjust the separation distance 42 during the data acquisition time. For example, in certain embodiments, the stage assembly 29 modulates the separation distance 42 back and forth along the Z axis during the data acquisition time.

It should be noted that the sample stage mover 29B can be designed to move the stage 29A along the X, Y, and Z axes and about the X, Y, and Z axes (six degrees of freedom). Alternatively, the stage mover 29B can be designed to move the stage 29A with less than six degrees of freedom. As non-exclusive examples, the stage mover 29B can include one or more linear motors, planar motors, piezoelectric actuators, voice coil motor, or other types of actuators.

As provided herein, the present invention provides that the separation distance 42 between the sample 10 and the last optical element 24A is adjusted during the data acquisition time. Thus, instead of or in addition to moving the sample 10 relative to the last optical element 24A, the last optical element 24A can be moved relative to a stationary sample 10 or a moving sample 10 to adjust the separation distance 42 during the data acquisition time.

For example, the imaging optical assembly 24 can include an optical stage mover assembly 24C retains and positions the entire imaging optical assembly 24 or a portion thereof, e.g. the last optical element 24A. In certain embodiments, the optical stage mover assembly 24C includes an optical stage 24D (that retains the entire imaging optical assembly 24 or a portion thereof, e.g. the last optical element 24A), and an optical stage mover 24E that selectively moves the optical stage 24D and the last optical element 24A under the control of the control system 30.

Additionally, the optical stage mover assembly 24C can include an optical measurement system 24F (e.g. one or more encoders, interferometers, a capacitance sensor, or another type of sensors) that monitors the position of the optical element 24A relative to the sample 10 or another reference and provides that information to the control system 30. This allows for the closed loop control of the optical stage mover assembly 24C with the control system 30. Stated in another fashion, the optical stage measurement system 24F can provide feedback that relates to the separation distance 42, and the control system 30 can use this feedback to control the optical stage mover assembly 24C in a closed loop fashion.

It should be noted that the stage 24D, the optical stage mover 24E, and the optical measurement system 24F are illustrated as simplified boxes, but will have a much different design that than illustrated in FIG. 1.

In one non-exclusive embodiment, the optical stage mover 24E is controlled to move the entire imaging optical assembly 24 or a portion thereof, e.g. the last optical element 24A, along the beam path 16B during the data acquisition time in which the image sensor 28 is controlled to construct the two-dimensional image 13A, 13B, 13C. For example, in certain embodiments, the optical stage mover assembly 24C modulates the separation distance 42 back and forth along the Z axis during the data acquisition time.

It should be noted that the optical stage mover 24E can be designed to move the last optical element 24A along the X, Y, and Z axes and about the X, Y, and Z axes (six degrees of freedom). Alternatively, the optical mover 24E can be designed to move with less than six degrees of freedom. As non-exclusive examples, the optical stage mover 24E can include one or more linear motors, planar motors, piezoelectric actuators, voice coil motor, or other types of actuators.

In FIG. 1, the optical mover assembly 24C moves the entire imaging optical assembly 24. Alternatively, for example, the optical mover assembly 24C can be designed to move the last optical element 24A relative to the rest of the imaging optical assembly 24. This design will work as long as the lenses in the imaging optical assembly 24 are design.

Figure 2A:
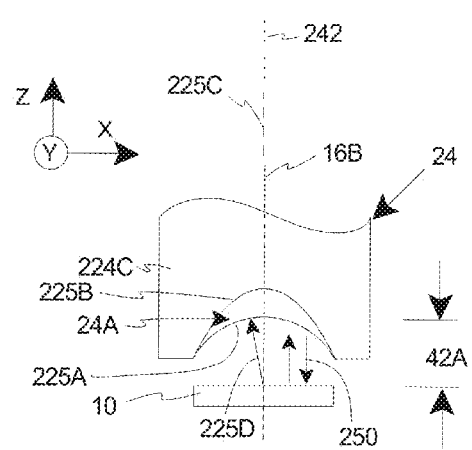
FIG. 2A and FIG. 2B are simplified illustrations of a sample and an optical element at alternative separation distances.
Figure 2B:
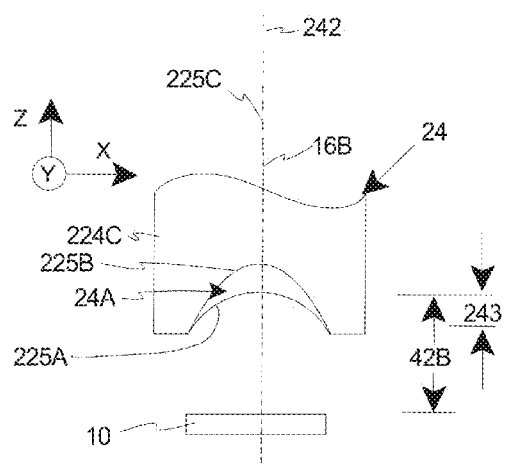

FIG. 2A and FIG. 2B are simplified illustrations of the sample 10 and a portion of the objective lens assembly 24 at different times during the capturing of a spectral image 13A-13C (illustrated in FIG. 1). In this embodiment, the objective lens assembly 24 includes the front, refractive optical element 24A and a portion of a lens housing 224C that retains the front, refractive optical element 24A. In FIG. 2A, the front, refractive optical element 24A is spaced apart a first separation distance 42A from the sample 10 along the beam path 16B. Further, in FIG. 2B, the front, refractive optical element 24A is spaced apart a second separation distance 42B from the sample 10 along the beam path 16B that is different from the first separation distance 42A. The distance between the first separation distance 42A and the second separation distance 42B can be referred to a modulation distance 243 (or "modulation" or "Δz"). The modulation distance 243 has an amplitude and profile.

In one embodiment, the front, refractive optical element 24A is disk shaped and includes (i) a curved, front element surface 225A that faces the sample 10 and that is closest to the sample 10; (ii) a curved, rear element surface 225B that faces away from the sample 10; and (iii) an element central axis 225C. As provided herein, the sample 10 and/or the refractive optical element 24A is moved along a modulation axis 242 so that the separation distance 42A, 42B is modulated along the modulation axis 242. Further, the modulation axis 242 is coaxial with the element central axis 225C and the central beam path 16B (e.g. the central beam propagation axis of the modified beam).

In certain embodiments, the front element surface 225A is curved and has a radius 225D that is approximately equal to the separation distance 42A. It should be noted that the front element surface 225A and the sample 10 have a small but finite reflectivity to light at or near the wavelengths of interest. In certain embodiments, the element surfaces 225A, 225B are coated to reduce the reflectivity.

FIG. 2A also includes opposite pointing arrows 250 that represent the standing waves being created (light bouncing back and forth) between front element surface 225A and the sample 10.

As provided herein, the optical mover assembly 24C (illustrated in FIG. 1) and/or the stage mover assembly 29 (illustrated in FIG. 1) are used to modulate the separation distance 42A, 42B during the data acquisition time of each image 13A-13C (illustrated in FIG. 1). The amplitude, frequency, and rate of modulation 242 during the data acquisition time can vary.

The modulation can have any waveform shape, such as a triangular, square, sinusoid or addition of an arbitrary set of sinusoids of varying amplitude, frequency, and phase. The frequency of the modulation can be between one times and 100 times the frame acquisition rate of the image sensor 28 (e.g. between 30 and 3000 Hz for an image sensor acquiring frames at 30 fps). As non-exclusive examples, the modulation frequency can be approximately thirty hertz, sixty hertz, or one hundred and twenty hertz. Alternatively, the modulation frequency can be non-integral multiples of the frame rate, e.g. approximately 131, 173, 180, or 210 hertz. As non-exclusive examples, the frequency of modulation can be at least approximately 1, 2, 3, 4, 5, 6, 7, 8, 9, 10, or more times the frame rate of the image sensor 28.

In alternative, non-exclusive examples, the amplitude of the modulation can be at least approximately 1, 2, 2.5, 3, 3.5, 4, 4.5, 5, 6, or 7 microns. Further, the amplitude of the modulation can be varied according to the wavenumber of the illumination beam 16. Stated in another fashion, the control system 30 can adjust an amplitude of the modulation distance 243 as a function of wavelength of the illumination beam 16. As non-exclusive examples, (i) when illuminating the sample 10 with an illumination beam 16 having a first center wavelength, a first modulation distance can be utilized during the capturing of the first spectral image 13A; (i) when illuminating the sample 10 with an illumination beam 16 having a second center wavelength, a second modulation distance can be utilized during the capturing of the second spectral image 13B; and (iii) when illuminating the sample 10 with an illumination beam 16 having a third center wavelength, a third modulation distance can be utilized during the capturing of the third spectral image 13C. In this example, the first, second and third center wavelengths are all different, and the first, second, and third modulation distances are all different.

Figure 2C:
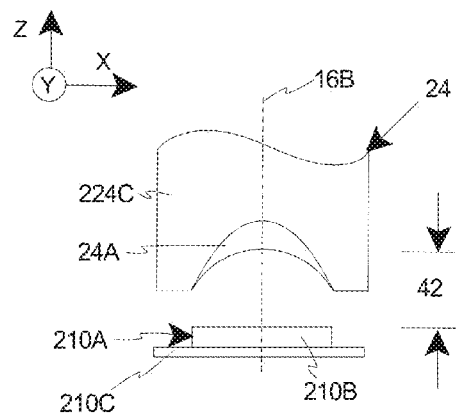
FIG. 2C and FIG. 2D are simplified illustrations of another sample and the optical element.

FIG. 2C is a simplified illustration of another embodiment of the sample 210A and a portion of the objective lens assembly 24, including the front, refractive optical element 24A and a portion of the lens housing 224C that retains the front, refractive optical element 24A. In FIG. 2C, the front, refractive optical element 24A is spaced apart a separation distance 42 from the sample 210A along the beam path 16B. In FIG. 2C, the sample 210A includes the specimen 210B that is being analyzed and a slide 210C that retains the specimen 210B. If the spectral imaging device 12 (illustrated in FIG. 1) is being used in the transmission mode, the slide 210C is designed to be transmissive to the wavelengths of illumination beam 16. Alternatively, if the spectral imaging device 12 is being used in the reflection mode, the slide 210C is designed to be reflective to the illumination beam 16.

Figure 2D:
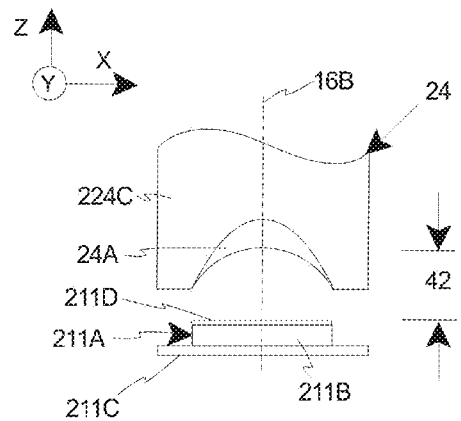

FIG. 2D is a simplified illustration of another embodiment of the sample 211A and a portion of the objective lens assembly 24, including the front, refractive optical element 24A and a portion of the lens housing 224C that retains the front, refractive optical element 24A. In FIG. 2D, the front, refractive optical element 24A is spaced apart a separation distance 42 from the sample 211A along the beam path 16B. In FIG. 2D, the sample 211A includes the specimen 211B that is being analyzed and two slides 211C, 211D. In this embodiment, the specimen 211B is positioned between the lower slide 211C and the upper slide 211D. If the spectral imaging device 12 (illustrated in FIG. 1) is being used in the transmission mode, each slide 211C, 211D is designed to be transmissive to the wavelengths of the illumination beam 16. Alternatively, if the spectral imaging device 12 is being used in the reflection mode, the lower slide 211C is designed to be reflective to the wavelengths of the illumination beam 16, and the upper slide 211D is designed to be transmissive to the wavelengths of the illumination beam 16.

As provided above, the amplitude, frequency, and rate of modulation during the data acquisition time can vary. FIGS. 3A, 3B, 3C, 3D, 3E, and 3F are simplified, non-exclusive illustrations of alternative modulation profiles versus time. In each example, the modulation distance (and the corresponding separation distance) varies during a data acquisition time 346 for each capture time. It should be noted that the system can be controlled so that the modulation profile has almost any arbitrary waveform shape.

Figure 3A:
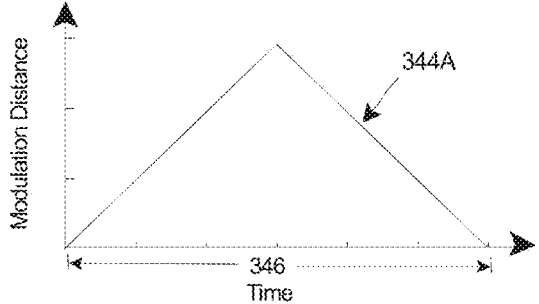
FIGS. 3A, 3B, 3C, 3D, 3E, and 3F are simplified, illustrations of alternative modulation profiles.

FIG. 3A illustrates a non-exclusive example of a first modulation profile 344A that illustrates how the modulation distance can be varied over time. In this example, the first modulation profile 344A has a triangular shaped waveform.

Figure 3B:
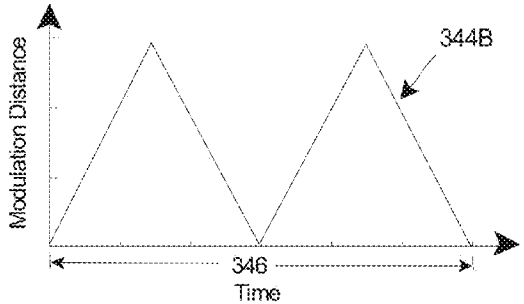

FIG. 3B illustrates a non-exclusive example of a second modulation profile 344B that illustrates how the modulation distance can be varied over time. In this example, the second modulation profile 344B also a triangular waveform, but the frequency has been increased from the first modulation profile 344A illustrated in FIG. 3A.

Figure 3C:
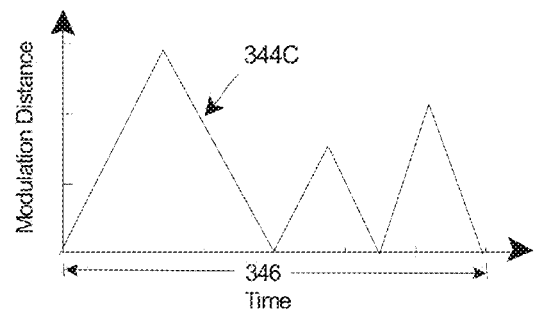

FIG. 3C illustrates a non-exclusive example of a third modulation profile 344C that illustrates how the modulation distance can be varied over time. In this example, the third modulation profile 344C also has a triangular waveform, but the frequency and amplitude are varied over the third modulation profile 344C. Further, the shape can be varied over the data acquisition time 346

Figure 3D:
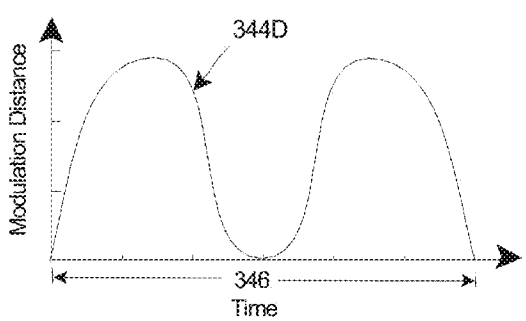

FIG. 3D illustrates a non-exclusive example of a fourth modulation profile 344D that illustrates how the modulation distance can be varied over time. In this example, the fourth modulation profile 344D has a sinusoidal waveform.

Figure 3E:
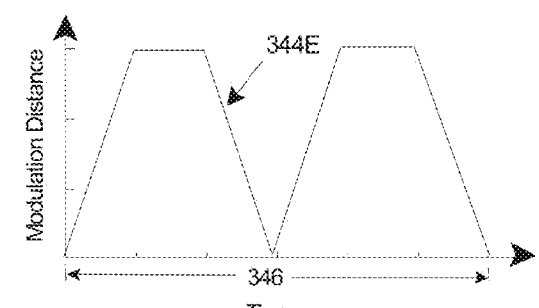

FIG. 3E illustrates a non-exclusive example of a fifth modulation profile 344E that illustrates how the modulation distance can be varied over time. In this example, the fifth modulation profile 344E has a somewhat square shaped waveform.

Figure 3F:
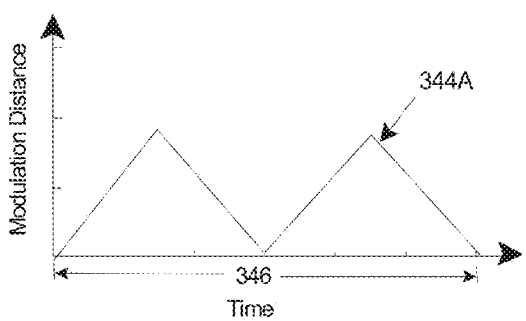

FIG. 3F illustrates a non-exclusive example of a sixth modulation profile 344F. In this example, in the sixth modulation profile 344F has a triangular shape similar to the second modulation profile 344B illustrated in FIG. 3B. However, the amplitude of the sixth modulation profile 344F is different.

It should be noted that the simplified, examples illustrated in FIGS. 3A-3F are non-exclusive examples and that the actual modulation profiles 344A-344F can be much different than these examples.

Figure 4A:
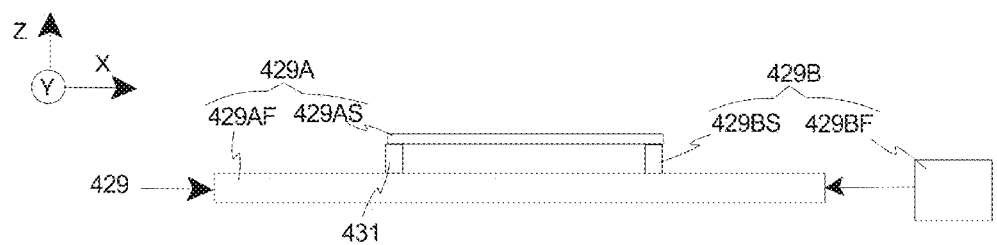
FIG. 4A is a simplified side view.
Figure 4B:
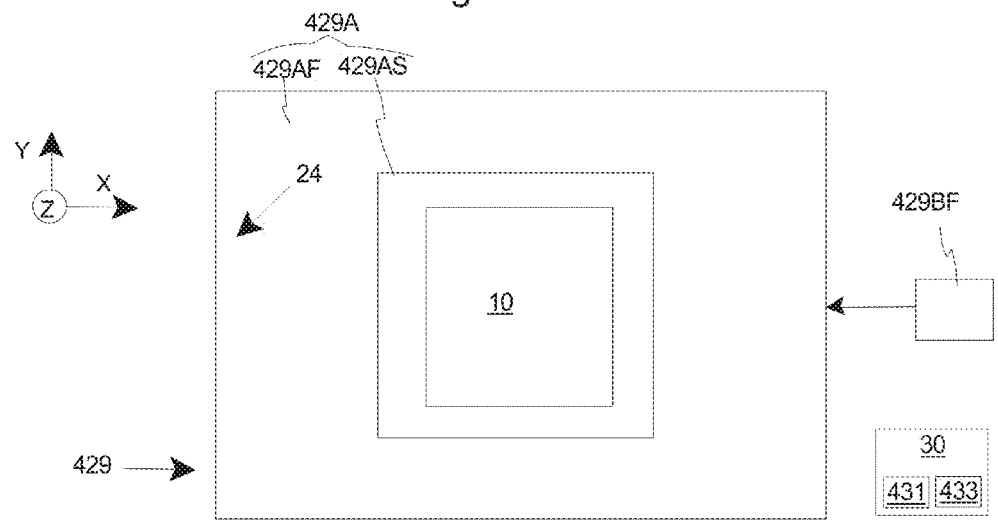
FIG. 4B is a simplified top view.
Figure 4C:
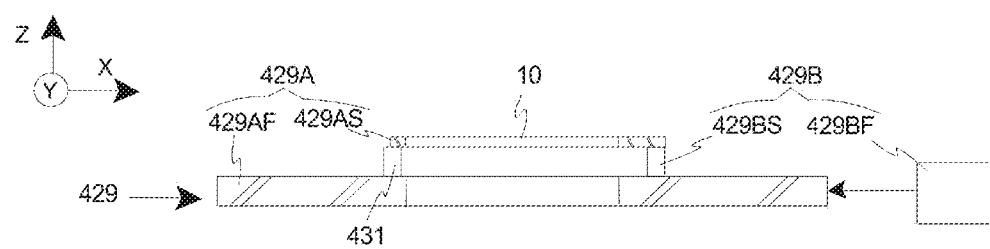
FIG. 4C is a cut-away view of a sample stage mover assembly.

FIG. 4A is a simplified side view, FIG. 4B is a simplified top view, and FIG. 4C is a cut-away view of a non-exclusive example of a sample stage mover assembly 429 that can be controlled to modulate the separation distance 42 (illustrated in FIG. 1) by moving the sample 10 along the Z axis. In this embodiment, the sample stage 429A includes a first stage 429AF and a second stage 428AS that retains the sample 10. Further, the sample stage mover 429B includes a first stage mover 429BF (illustrated as a box) and a second stage mover 429BS (illustrated as a box). With this design, the first stage mover 429BF can be designed to make relatively large scale movements of the first stage 429AF, and the second stage mover 429BS can be used to make relatively small scale movements of the second stage 428AS and the sample 10.

For example, each stage mover 429BF, 429BS can be designed to move the respective stage 429AF, 429AS along one or more of the X, Y, and Z axes and/or about one or more of the X, Y, and Z axes. As a non-exclusive example, the first stage mover 428BF can be designed to move the first stage 429AF with six degrees of freedom, while the second stage mover 428BS can be designed to move the second stage 429AS rapidly and accurately along the Z axis to modulate the separation distance 42 during the data acquisition time. Each stage mover 429BF, 429BS can include one or more linear motors, planar motors, piezoelectric actuators, voice coil motor, or other types of actuators.

Additionally, the second stage 429AS can be coupled to the first stage 429AF using one or more mechanical flexures 431.

As described above, the control system 30 (illustrated in FIG. 4B) can control the sample stage mover assembly 429. For example, the control system 30 can include an electrical amplifier 431 (illustrated as a box), and a waveform generator 433 (illustrated as a box).

Figure 5A:
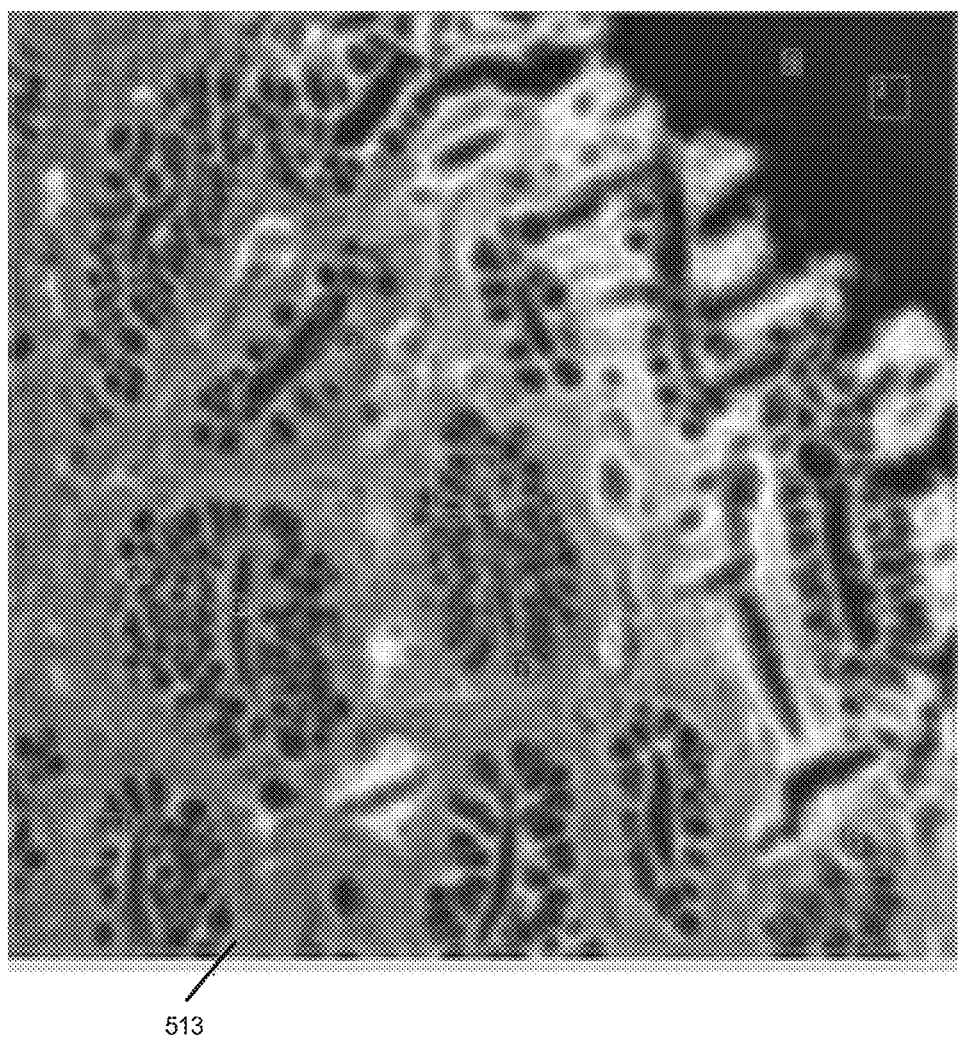
FIG. 5A is a simplified illustration of a spectral image captured without modulation.

FIG. 5A is a simplified illustration of a spectral image 513 of a tissue sample that was captured using the spectral imaging device 12 of FIG. 1 without modulating the separation distance during the capturing of the spectral image 513. In this example, the spectral image 513 was captured while the sample was being illuminated with an illumination beam having a center wavenumber of 1656 cm$^{-1}$ (v=1656 cm$^{-1}$). As provided herein, the spectral image 513 is slightly blurry because of the standing waves in the spectral imaging device.

Figure 5B:
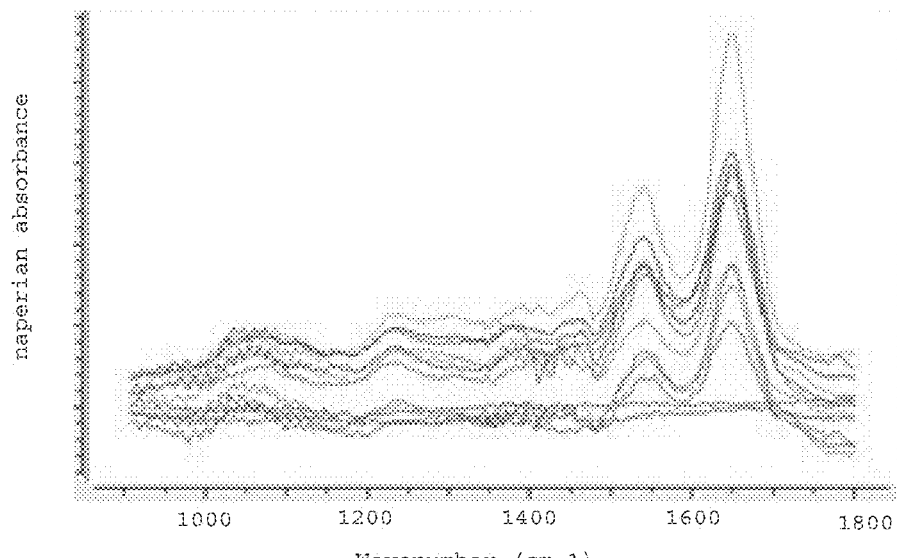
FIG. 5B is a simplified illustration of a graph.
Figure 5C:
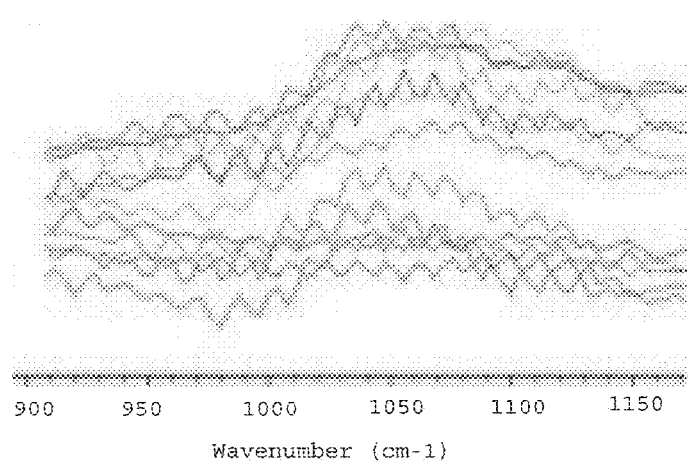
FIG. 5C is a simplified illustration of a portion of the graph of FIG. 5B.

FIG. 5B is a graph that illustrates naperian absorbance versus wavenumber for the spectral imaging device 12 without modulation for twelve different regions (each represented by a different curve) of the image sensor. FIG. 5C is a simplified illustration of a portion of the graph (the lower wavenumber region) of FIG. 5B. FIG. 5C illustrates that without modulation, there are high frequency spectral oscillations. These high frequency spectral oscillations are caused by standing waves and will adversely influence the quality of the spectral image 513.

Figure 6A:
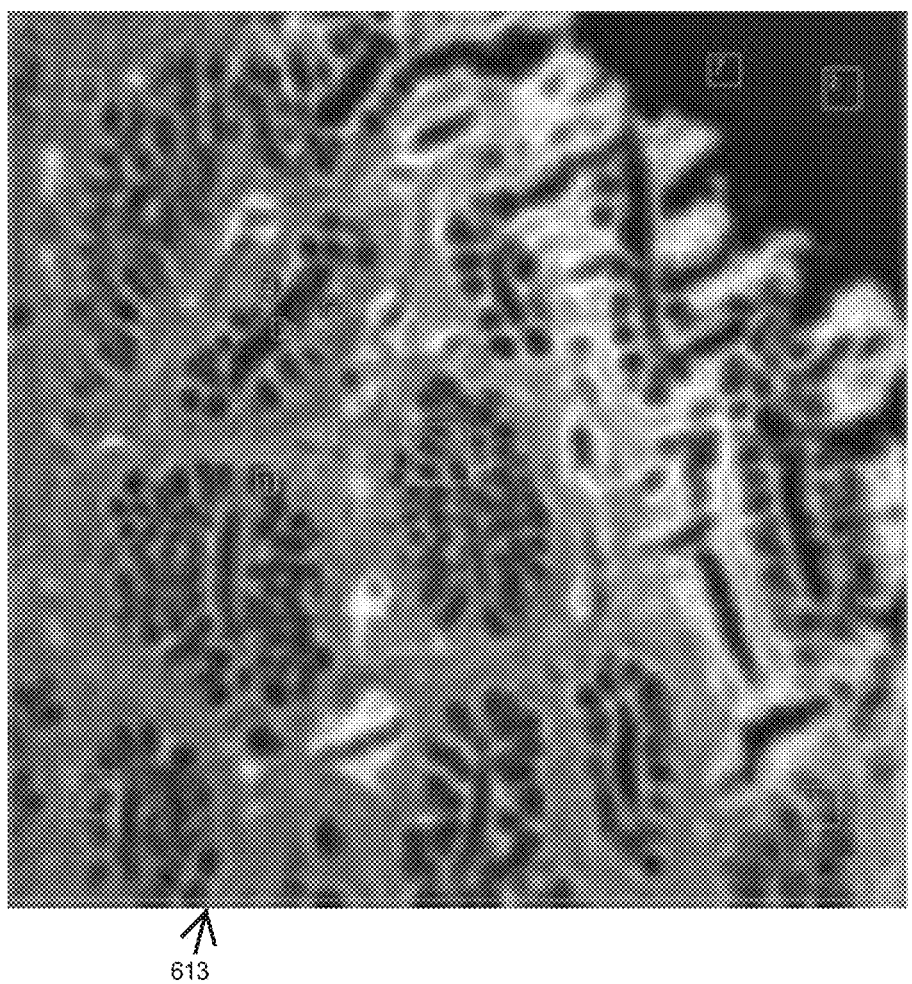
FIG. 6A is a simplified illustration of a spectral image captured with modulation.

FIG. 6A is a simplified illustration of a spectral image 613 of a tissue sample that was captured using the spectral imaging device 12 of FIG. 1 while modulating the separation distance during the capturing of the spectral image. In this example, the spectral image 613 was captured while the sample was being illuminated with an illumination beam having a center wavenumber of 1656 cm$^{-1}$ ($\bar{v}$=1656 cm$^{-1}$), and the separation distance was modulated with a triangular shaped wave having a frequency of one hundred hertz, with an amplitude of 4.5 microns.

It should be noted that the spectral image 613 of FIG. 6A is crisper than the spectral image 513 of FIG. 5A because the modulation of the separation distance frustrates the standing wave.

Figure 6B:
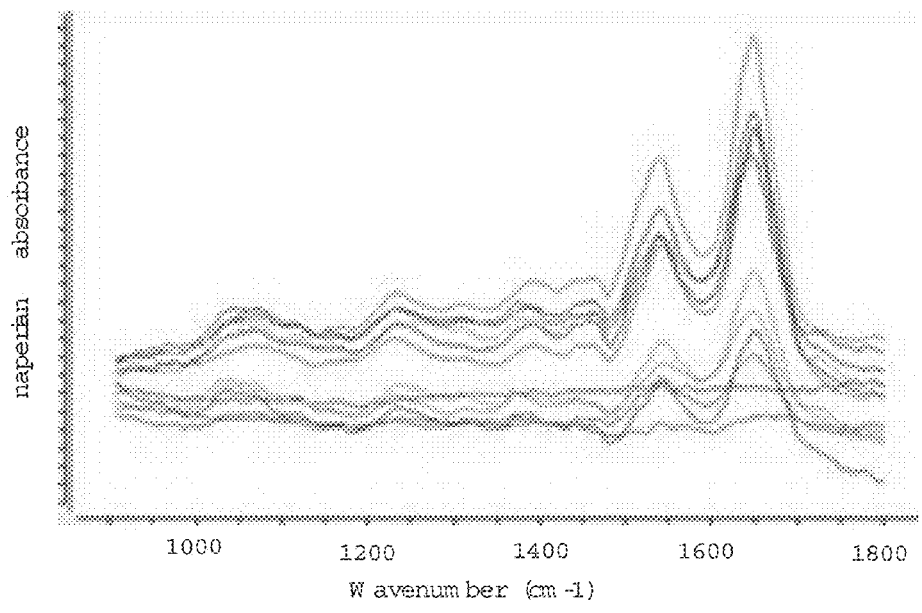
FIG. 6B is a simplified illustration of a graph.
Figure 6C:
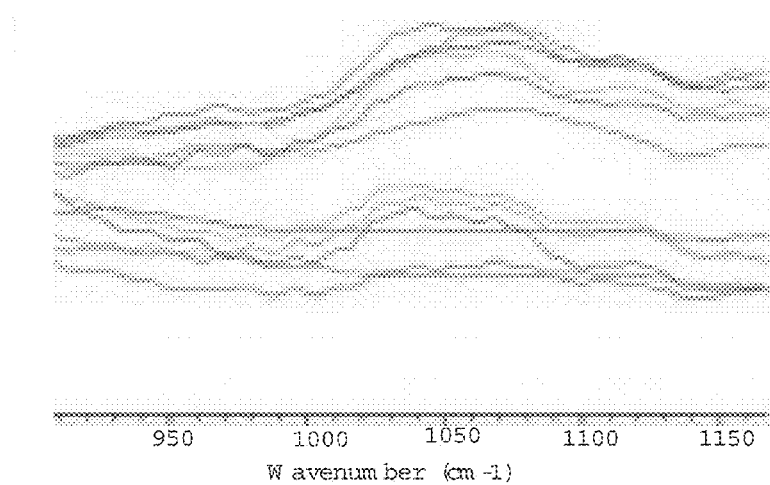
FIG. 6C is a simplified illustration of a portion of the graph of FIG. 6B.

FIG. 6B is a graph that illustrates naperian absorbance versus wavenumber for the spectral imaging device 12 while modulating the separation distance for twelve different regions (each represented by a different curve) of the image sensor. FIG. 6C is a simplified illustration of a portion of the graph (the lower wavenumber region) of FIG. 6B. FIG. 6C illustrates that with modulation, the high frequency spectral oscillations are reduced as compared to FIG. 5C. Thus, the modulation of the separation distance reduces the high frequency spectral oscillations caused by standing waves and improves the quality of the spectral image 613.

Figure 7A:
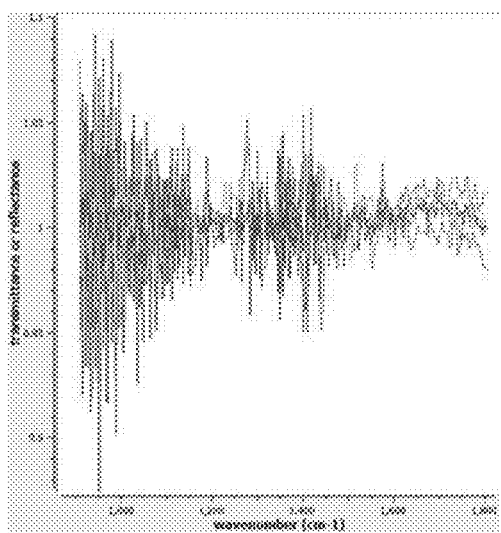
FIGS. 7A and 7B are graphs that illustrate transmittance or reflectance versus wavenumber.
Figure 7B:
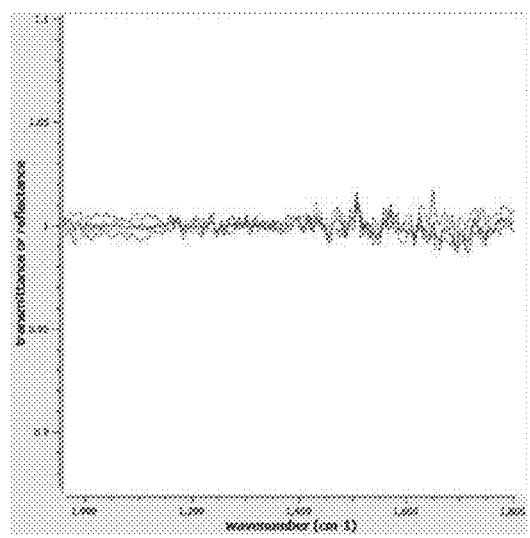

FIG. 7A is a graph that illustrates transmittance or reflectance versus wavenumber for six different regions (each represented by a different curve) of the image sensor, for the spectral imaging device 12 without modulation. In contrast, FIG. 7B is a graph that illustrates transmittance or reflectance versus wavenumber for six different regions (each represented by a different curve) of the image sensor, for the spectral imaging device 12 with modulation of the separation distance. Comparing FIGS. 7A and 7B, the spectral performance is significantly better with modulation of the separation distance.

Figure 8A:
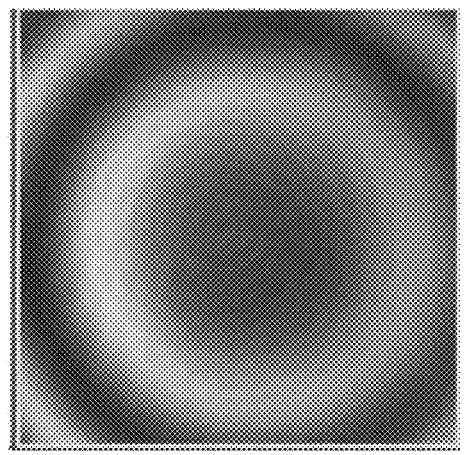
FIGS. 8A-8D are illustrations of patterns of the standing wave.
Figure 8B:
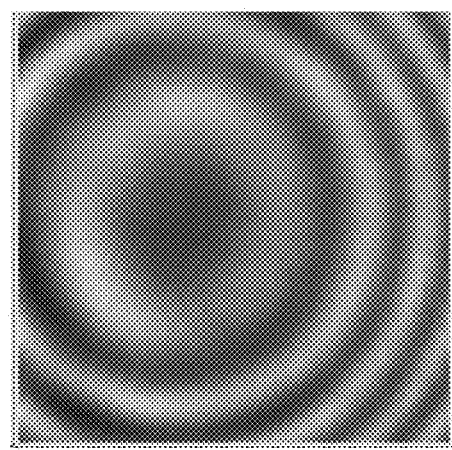
Figure 8C:
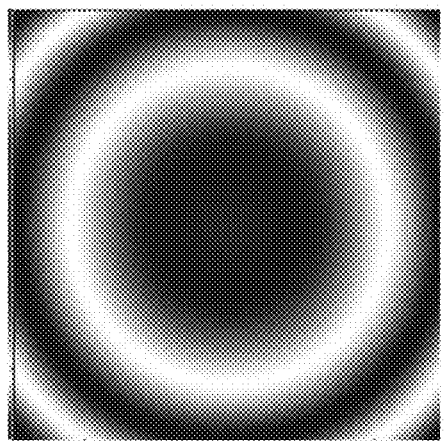
Figure 8D:
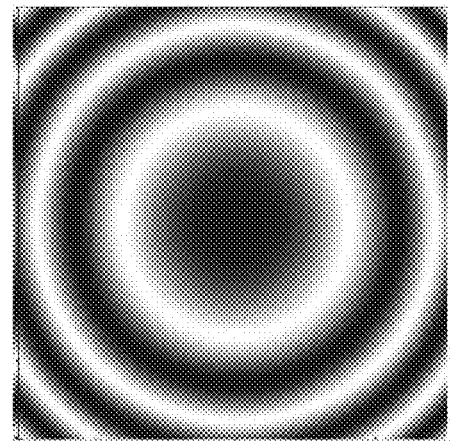

FIG. 8A is an illustration of an actual pattern of the standing wave at a wavenumber of 996 cm$^{-1}$ ($\bar{v}$=996 cm$^{-1}$). Further, FIG. 8B is an illustration of an actual pattern of the standing wave at a wavenumber of 1588 cm$^{-1}$ ($\bar{v}$=1588 cm$^{-1}$). FIG. 8C is an illustration of a modeled pattern of the standing wave at a wavenumber of 996 cm$^{-1}$ ($\bar{v}$=996 cm$^{-1}$). Further, FIG. 8D is an illustration of a modeled pattern of the standing wave at a wavenumber of 1588 cm$^{-1}$ ($\bar{v}$=1588 cm$^{-1}$). The curved front element surface 225A of the refractive, optical element 224A results in a radial pattern of the standing wave. Further, the standing wave varies according to wavenumber.

Figure 9:
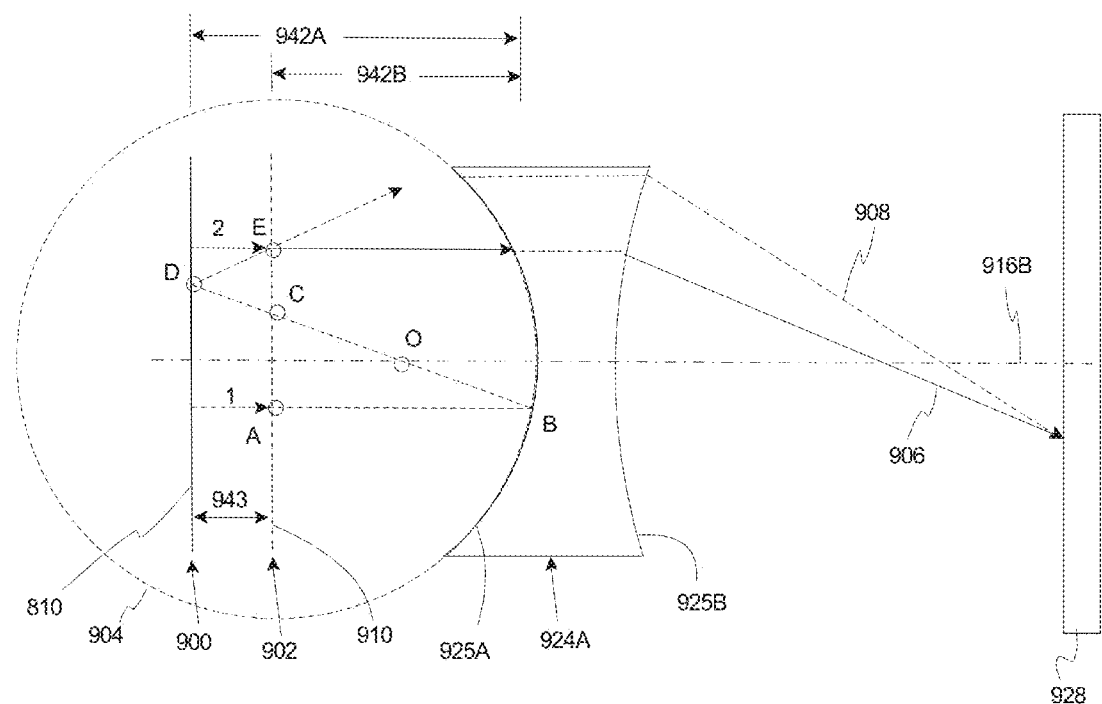
FIG. 9 is a simplified illustration of a portion of the spectral imaging device.

FIG. 9 is a simplified illustration (i) a refractive, optical element 924A including a front element surface 925A, and a rear element surface 925B; the sample 910 at a first position (illustrated with a solid line) 900 and at a second position 902 (illustrated with a dashed line) spaced apart the modulation distance 943 ($\Delta Z$); and an image sensor 929. Further, a first separation distance 942A and a second separation distance 942B are also illustrated. FIG. 9 also includes a dashed circle 904 that highlights that curved front element surface 925A has a radius that is approximately equal to the separation distance 942A, 942B during the modulation. The center beam path 916B is also illustrated in FIG. 9.

Additionally, the optical path of first rays 906 (illustrated with a solid line) from the sample 910 to the image sensor 929, and the optical path of second rays 909 (illustrated with a dashed line) from the sample 910 to the image sensor 929 are also illustrated in FIG. 9. The optical path length difference between the first rays 906 and the second rays 909 can be expressed as follows:

$$\Lambda = \overline{AB} + \overline{BC} + \overline{CD} + \overline{DE} = \overline{AB} + \overline{BC} + 2\overline{DE} \quad \text{(Equation 1)}$$

$$\Lambda = \sqrt{R^2 - h^2} + \sqrt{2h^2 + R^2} \pm 2\Delta z \sqrt{\frac{3h^2 + R^2}{R^2 - h^2}}. \quad \text{(Equation 2)}$$

In these equations an elsewhere, $\Lambda$ it the optical path length difference, h is the radial distance of the ray from the optical axis, and R is radius of curvature of the objective front lens surface. The locations of A, B, C, D, and E are illustrated in FIG. 9. In FIG. 9, O is the coordinate origin which is shown to be coincident with the center of curvature of the objective front lens surface.

As provided herein, in certain embodiments, the fringe pattern can be driven through a complete 2 pi cycle by adjusting the separation distance (delta Z) relative to the objective front surface by the following amount:

$$2\pi * \bar{v} * \frac{d\Lambda}{dz} \Delta z = 2\pi \quad \text{(Equation 3)}$$

$$\frac{d\Lambda}{dz} = 2\sqrt{\frac{3h^2 + R^2}{R^2 - h^2}} \quad \text{(Equation 4)}$$

$$\Delta z = \frac{1}{2\bar{v}} = 2\sqrt{\frac{R^2 - h^2}{3h^2 - R^2}} \quad \text{(Equation 5)}$$

$$\Delta z = \frac{1}{2\bar{v}\sqrt{\frac{3h^2 + R^2}{R^2 - h^2}}} \approx \frac{1}{2\bar{v}}. \quad \text{(Equation 6)}$$

In these equations and elsewhere, $\bar{v}$ is wavenumber. Equation 3 sets the condition for how much the optical path length must change in order to achieve one full cycle of the standing wave. Equation 4 is the rate of change of optical path length difference for a change in physical separation distance between the objective front lens surface and the sample surface. Equations 5 and 6 describe the amount of separation distance change that must occur to achieve a full cycle of the standing wave.

Basically, these equations can be utilized to determine the amplitude of the modulation that is necessary to achieve one period of fringe pattern change. Using these equations, if the sample is illuminated at wavenumber 1500 cm$^{-1}$ ($\bar{v}$=1500 cm$^{-1}$), the separation distance can be modulated at an amplitude of 3.33 microns ($\Delta z$=3.33 microns) to achieve one period of fringe pattern change and frustrate the standing waves. Similarly, if the sample is illuminated at wavenumber 1000 cm$^{-1}$ ($\bar{v}$=1000 cm$^{-1}$), the separation distance can be modulated at an amplitude of five microns ($\Delta z$=5 microns) to achieve one period of fringe pattern change and frustrate the standing waves.

Accordingly, in certain embodiments, the control system adjusts an amplitude of the modulation distance as a function of wavelength of the illumination beam to frustrate the standing waves. Generally speaking, in certain embodiments, the amplitude of the modulation distances needs to be increased as the wavenumber is decreased.

Figure 10A:
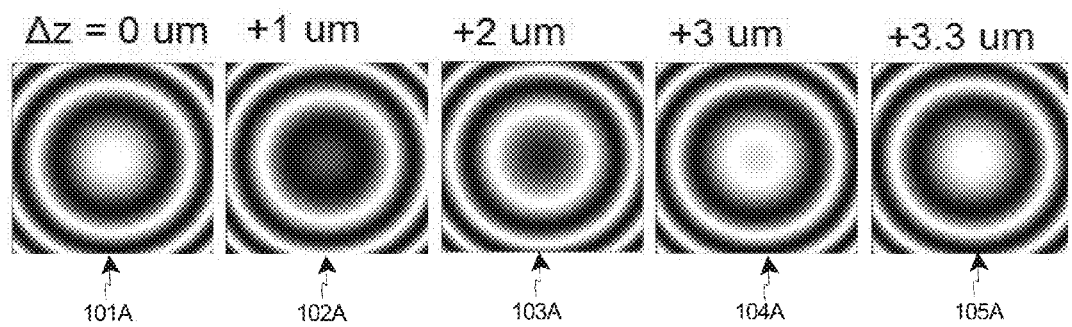
FIGS. 10A and 10B illustrate a plurality of patterns of the standing wave at alternative modulation distances.

FIG. 10A illustrates a plurality of patterns of the standing wave at alternative modulation distances ("Δz") with sample being illuminated with an illumination beam having a center wavelength of 1500 cm$^{-1}$ (v=1500 cm$^{-1}$). More specifically, FIG. 10A includes (i) a first pattern 101A at a modulation distance of zero (Δz=0 microns); (ii) a second pattern 102A at a modulation distance of one micron (Δz=1 microns); (iii) a third pattern 103A at a modulation distance of two microns (Δz=2 microns); (iv) a fourth pattern 104A at a modulation distance of three microns (Δz=3 microns); and (v) a fifth pattern 105A at a modulation distance of 3.3 microns (Δz=3.3 microns). As illustrated herein, the first pattern 101A and the fifth pattern 105A are approximately the same. Thus, the pattern can be driven through a complete 2 pi cycle by sufficiently modulating the separation distance. In this example, at a center wavelength of 1500 cm$^{-1}$, the pattern can be driven through a complete 2 pi cycle by sufficiently modulating the separation distance by 3.3 microns.

Figure 10B:
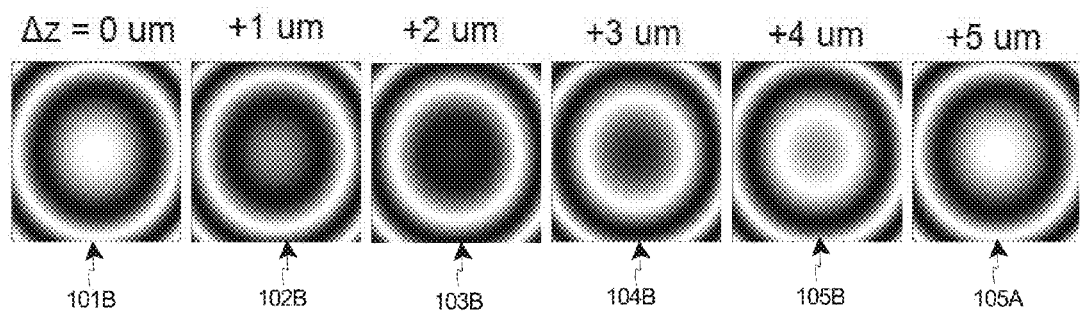

FIG. 10B illustrates a plurality of patterns of the standing wave at alternative modulation distances ("Δz") with sample being illuminated with an illumination beam having a center wavelength of 1000 cm$^{-1}$ (v=1000 cm$^{-1}$). More specifically, FIG. 10B includes (i) a first pattern 101B at a modulation distance of zero (Δz=0 microns); (ii) a second pattern 102B at a modulation distance of one micron (Δz=1 microns); (iii) a third pattern 103B at a modulation distance of two microns (Δz=2 microns); (iv) a fourth pattern 104B at a modulation distance of three microns (Δz=3 microns); (v) a fifth pattern 105B at a modulation distance of four microns (Δz=4 microns); and (v) a sixth pattern 106B at a modulation distance of five microns (Δz=5 microns). As illustrated herein, the first pattern 101B and the sixth pattern 105B are approximately the same. Thus, the pattern can be driven through a complete 2 pi cycle by sufficiently modulating the separation distance. In this example, at a center wavelength of 1000 cm$^{-1}$, the pattern can be driven through a complete 2 pi cycle by sufficiently modulating the separation distance by five microns.

Figure 11A:
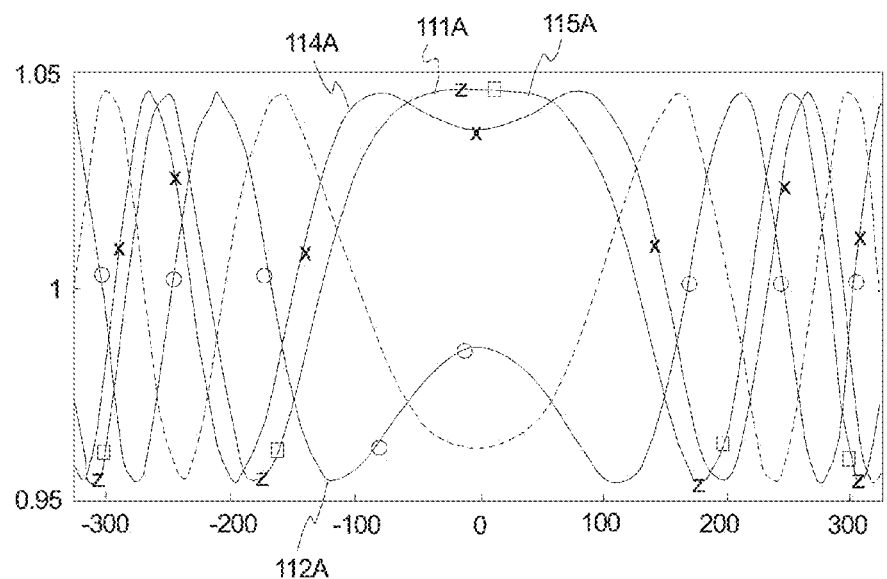
FIGS. 11A and 11B are cross-sectional views of an imaged fringed pattern as a function of modulation distance.

FIG. 11A is cross-section of an imaged fringed pattern as a function of modulation distance ("Δz") with sample being illuminated with an illumination beam having a center wavelength of 1500 cm$^{-1}$. More specifically, FIG. 11A includes (i) a first pattern curve 111A (line with squares) at a modulation distance of zero (Δz=0 microns); (ii) a second pattern curve 112A (line with circles) at a modulation distance of one micron (Δz=1 microns); (iii) a third pattern curve 113A (dashed line) at a modulation distance of two microns (Δz=2 microns); (iv) a fourth pattern curve 114A (line with "x's") at a modulation distance of three microns (Δz=3 microns); and (v) a fifth pattern curve 115A (line with "z's") at a modulation distance of 3.3 microns (Δz=3.3 microns). In this example, the first pattern curve 111A and the fifth pattern curve 115A approximately overlap.

Figure 11B:
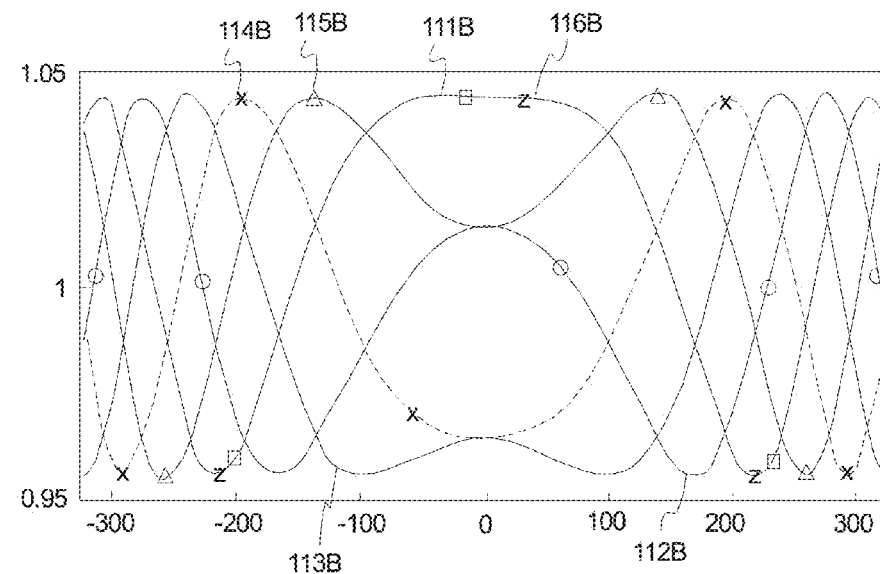

FIG. 11B is cross-section of an imaged fringed pattern as a function of modulation distance ("Δz") with sample being illuminated with an illumination beam having a center wavelength of 1000 cm$^{-1}$. More specifically, FIG. 11B includes (i) a first pattern curve 111B (line with squares) at a modulation distance of zero (Δz=0 microns); (ii) a second pattern curve 112B (line with circles) at a modulation distance of one micron (Δz=1 microns); (iii) a third pattern curve 113B (dashed line) at a modulation distance of two microns (Δz=2 microns); (iv) a fourth pattern curve 114B (line with "x's") at a modulation distance of three microns (Δz=3 microns); (v) a fifth pattern curve 115B (line with triangles) at a modulation distance of 4 microns (Δz=4 microns); and (vi) a sixth pattern curve 116B (line with "z's") at a modulation distance of 5 microns (Δz=5 microns). In this example, the first pattern curve 111B and the sixth pattern curve 116B approximately overlap.

While the particular spectral imaging device 12 as herein shown and disclosed in detail is fully capable of obtaining the objects and providing the advantages herein before stated, it is to be understood that it is merely illustrative of some of the presently preferred embodiments of the invention and that no limitations are intended to the details of construction or design herein shown other than as described in the appended claims.

What is claimed is:

1. A spectral imaging device for generating a two-dimensional spectral image of a sample, the spectral imaging device comprising:
    an image sensor that includes a two-dimensional array of sensor elements that are used to acquire data to construct the two-dimensional spectral image during a data acquisition time;
    an illumination source that generates an illumination beam that illuminates the sample to create a modified beam that follows a beam path from the sample to the image sensor;
    a refractive, optical element that is positioned along the beam path between the sample and the image sensor, the refractive optical element being spaced apart a separation distance from the sample along the beam path;
    a mover assembly that moves at least one of the sample and the optical element along the beam path to change the separation distance; and
    a control system that (i) controls the illumination source to generate the illumination beam during the data acquisition time, (ii) controls the mover assembly to change the separation distance during the data acquisition time, and (iii) controls the image sensor to capture the data during the data acquisition time.

2. The spectral imaging device of claim 1 wherein the mover assembly moves the sample relative to the refractive optical element along the beam path to adjust the separation distance.

3. The spectral imaging device of claim 1 wherein the mover assembly moves the refractive optical element relative to sample along the beam path to adjust the separation distance.

4. The spectral imaging device of claim 1 wherein the illumination source is tunable to adjust a center wavelength of the illumination beam.

5. The spectral imaging device of claim 4 wherein the illumination source is a tunable laser source and the illumination beam is a laser beam.

6. The spectral imaging device of claim 1 wherein the refractive, optical element includes a front element surface faces the sample.

7. The spectral imaging device of claim 6 wherein the front element surface is curved and has a radius that is approximately equal to the separation distance.

8. The spectral imaging device of claim 6 wherein the front element surface has a finite reflectivity to light near a center wavelength of the illumination beam.

9. The spectral imaging device of claim 1 wherein the control system controls the mover assembly to modulate the separation distance by a modulation distance during the data acquisition time that is at least approximately three microns.

10. The spectral imaging device of claim 9 wherein the control system adjusts an amplitude of the modulation distance as a function of wavelength of the illumination beam.

11. The spectral imaging device of claim 1 wherein the control system controls the mover assembly to modulates the separation distance to have a frequency of at least approximately two times the data acquisition time.

12. The spectral imaging device of claim 1 wherein the mover assembly includes a piezoelectric actuator that adjusts the separation distance.

13. The spectral imaging device of claim 1 further comprising a measurement system that provides feedback that relates to the separation distance, and wherein the control system uses the feedback to control the mover assembly in a closed loop fashion.

14. A spectral imaging device for generating a two-dimensional spectral image of a sample, the spectral imaging device comprising:
an image sensor that includes a two-dimensional array of sensor elements that are used to acquire data to construct the two-dimensional spectral image during a data acquisition time;
a laser illumination source that generates a laser illumination beam that illuminates the sample to create a modified beam that follows a beam path from the sample to the image sensor; the illumination source being tunable to adjust a center wavelength of the illumination beam;
a refractive, optical element that is positioned along the beam path between the sample and the image sensor, the refractive optical element being spaced apart a separation distance from the sample along the beam path, the refractive, optical element including a front element surface faces the sample, the front element surface having a finite reflectivity to light near a center wavelength of the illumination beam;
a mover assembly that moves at least one of the sample and the optical element along the beam path to change the separation distance; and
a control system that (i) controls the illumination source to generate the illumination beam during the data acquisition time, (ii) controls the mover assembly to change the separation distance during the data acquisition time, and (iii) controls the image sensor to capture the data during the data acquisition time.

15. The spectral imaging device of claim 14 wherein the front element surface is curved and has a radius that is approximately equal to the separation distance.

16. The spectral imaging device of claim 14 wherein the control system controls the mover assembly to modulate the separation distance by a modulation distance during the data acquisition time that is at least approximately three microns.

17. The spectral imaging device of claim 14 wherein the control system controls the mover assembly to modulate the separation distance by a modulation distance during the data acquisition time, and wherein the control system adjusts an amplitude of the modulation distance as a function of wavelength of the illumination beam.

18. The spectral imaging device of claim 17 wherein the mover assembly is controlled so that the separation distance has a modulation distance that is defined by the following equation:

$$\Delta z = \frac{1}{2\bar{v}} = 2\sqrt{\frac{R^2 - h^2}{3h^2 - R^2}}$$

where $\Delta z$ is the modulation distance, $\bar{v}$ is wavenumber of the illumination beam, h is a radial distance of a ray from an optical axis of the refractive, optical element, and R is a radius of curvature of the refractive, optical element.

19. A method for generating a two-dimensional spectral image of a sample, the method comprising:
acquiring data with an image sensor that includes a two-dimensional array of sensor elements to construct the two-dimensional spectral image during a data acquisition time;
illuminating the sample with an illumination beam to create a modified beam that follows a beam path from the sample to the image sensor during the data acquisition time;
positioning a refractive, optical element along the beam path between the sample and the image sensor, the refractive optical element being spaced apart a separation distance from the sample along the beam path;
moving at least one of the sample and the optical element along the beam path to change the separation distance during the data acquisition time.

20. The method of claim 19 wherein the step of positioning includes the refractive, optical element having a front element surface faces the sample, and the front element surface has a finite reflectivity to light near a center wavelength of the illumination beam.

21. The method of claim 19 wherein the step of moving includes changing the separation distance by a modulation distance during the data acquisition time that is at least approximately three microns.

22. The method of claim 19 wherein the step of moving includes modulating the separation distance to have a frequency of at least approximately two times the data acquisition time.

* * * * *